United States Patent
Silva et al.

(10) Patent No.: US 9,051,580 B2
(45) Date of Patent: Jun. 9, 2015

(54) GENES AND METHODS FOR INCREASING DISEASE RESISTANCE IN PLANTS

(75) Inventors: Ana Claudia Rasera Silva, Sao Paulo (BR); Gustavo Adolfo Astúa Monge, Sao Paulo (BR)

(73) Assignee: MONSANTO DO BRASIL LTDA., São Paulo (BR)

( * ) Notice: Subject to any disclaimer, the term of this patent is extended or adjusted under 35 U.S.C. 154(b) by 216 days.

(21) Appl. No.: 12/991,412

(22) PCT Filed: May 8, 2009

(86) PCT No.: PCT/IB2009/005842
§ 371 (c)(1),
(2), (4) Date: Jan. 13, 2011

(87) PCT Pub. No.: WO2009/136293
PCT Pub. Date: Nov. 12, 2009

(65) Prior Publication Data
US 2011/0107459 A1     May 5, 2011

Related U.S. Application Data

(60) Provisional application No. 61/051,459, filed on May 8, 2008.

(51) Int. Cl.
    *C12N 15/29*      (2006.01)
    *C12N 15/82*      (2006.01)
    *C07K 14/415*     (2006.01)

(52) U.S. Cl.
    CPC .......... *C12N 15/8281* (2013.01); *C07K 14/415* (2013.01)

(58) Field of Classification Search
    USPC ........................................ 800/279; 536/23.6
    See application file for complete search history.

(56) References Cited

FOREIGN PATENT DOCUMENTS

WO    WO 03/068911 A2    8/2003

OTHER PUBLICATIONS

Close et al. Accession No. CB290728; deposited Feb. 28, 2003.*
Uratsu, S et al . Accession No. CK935579; deposited Mar. 19, 2004.*
Close et al. Accession No. CV885655; Nov. 22, 2004.*
International Search Report PCT/IB2009/005842 dated Jan. 7, 2010.
Database EMBL [Online] Apr. 6, 2004, "UCRCSO4_0003N16_r Ruby Orange Developing Flower cDNA Library Citrus sinensis cDNA clone CS_REb0003N16, mRNA sequence." XP002568337.
Database Biosis [Online] Biosciences Information Service, Philadelphia PA US; 2007, Guidetti-Gonzalez Simone et al., "Putative resistance genes in the CitEST database", XP002568339, 2007.
Z. Dheng et al., "Cloning and characterization of receptor kinase class disease resistance gene candidates in Citrus", Theor. Appl. Genet. (2003), 108: 53-61.
Z. Deng et al., "Cloning and characterization of NBS-LRR class resistance-gene candidate sequences in citrus", Theor. Appl. Genet. (2000) 101:814-822.
Z. Deng et al., "Construction of a bacterial artificial chromosome (BAC) library for citrus and identification of BAC contigs containing resistance gene candidates", Theor. Appl. Genet. (2001) 102:1177-1184.
Magnolia A. Campos et al., "PR gene families of citrus : Their organ specific-biotic and abiotic inducible expression profiles based on ESTs approach", Genetics & Molecular Biology, 30, 3 (suppl) 917-930 (2007).
Raol Andres Cernadas et al., "Transcriptional analysis of the sweet orange interaction with the citrus canker pathogens *Xanthomonas axonopodis* pv. *citri* and *Xanthomonas axonopodis* pv. *aurantifolii*", Molecular Plant Pathology, (2008) 9(5), 609-631.

* cited by examiner

*Primary Examiner* — Medina A Ibrahim
(74) *Attorney, Agent, or Firm* — Lowe Hauptman & Ham, LLP

(57) ABSTRACT

The present invention relates to the regulation of the natural defense system of plants through the introduction of foreign/native genes into plant cells, preferably into their genomes. More specifically, the methods relate to increasing *citrus* plant disease resistance by over-expressing genes involved in the innate plant defense system.

17 Claims, 7 Drawing Sheets

GENES AND METHODS FOR INCREASING DISEASE RESISTANCE IN PLANTS

CROSS-REFERENCE TO RELATED APPLICATION

This application claims priority to U.S. Provisional Application No. 61/051,459, filed May 8, 2008.

FIELD OF THE INVENTION

The present invention relates to the field of molecular biology and the regulation of the natural defense system of plants through the introduction of foreign/native genes into plant cells, preferably into their genomes. More specifically, the method relates to increasing *citrus* plant disease resistance by overexpressing genes involved in the innate plant defense system. The invention also relates to such genes.

INTRODUCTION

In nature, plants and animals are in permanent contact with a widely diverse array of microorganisms, though seldom does this association result in disease. This is due mainly to the existence of defense systems which, in the case of plants, lack the adaptive immune response common in the animal kingdom.

The ability of a plant to recognize a pathogen and activate an effective defense is often controlled by the interaction (direct or indirect) between the products of a plant resistance gene and a pathogen avirulence gene. Dangl and Jones, 2001, *Nature* 411, 826-33. As a consequence of this gene-for-gene interaction, the newly infected tissue may exhibit ion fluxes, the production of reactive oxygen species, salicylic acid (SA), nitric oxide, and increased expression of defense-associated genes, including those encoding pathogenesis-related (PR) proteins. Durrant and Dong, 2004, *Annu. Rev. Phytopathol.* 2004. 42:185-209. In addition, the cells surrounding the site(s) of pathogen entry usually undergo apoptotic-like cell death, thereby forming the necrotic lesions characteristic of the hypersensitive response (HR). Heath, 2000, *Plant Molecular Biology* 44: 321-34.

To date, several plant resistance genes (R genes) have been cloned and based on the structure of the proteins they encode, the genes are divided into several groups (Hammond-Kosack and Jones, 1997, Annu. Rev. Plant Physiol. Plant Molec. Biol. 48, 575-607). Most R genes encode cytoplasmic NB-LRR proteins, containing a nucleotide binding site (NB) and leucine-rich repeats (LRR). This group consists of genes encoding CC-NB-LRR proteins, containing a coiled-coil domain and genes that encode proteins that have a domain similar to mammalian Toll and interleukin (IL) receptors, the so-called TIR-NB-LRR proteins (Hammond-Kosack and Jones, 1997, supra).

Using such specific resistance genes in breeding programs for durable resistance is problematic since pathogens easily circumvent recognition by mutations in their avirulence factors, thereby preventing induction of active defense (Westerink et al., 2004, Mol. Microbiol. 54, 533-545). Similarity among resistance proteins (R proteins) suggests the existence of common resistance pathways (Shirasu and Schulze-Lefert, 2000, Plant Mol. Biol. 44, 371-385). Therefore, identification of additional genes required for resistance not only provides information on how such signaling pathways function but might also enable us to identify genes that play a more general role in resistance.

Despite the increasing information about disease resistance pathways, there is still a need to identify genes and proteins that can be used to create plants with durable, broad range disease resistance. It is an object of the invention to provide such nucleic acids, proteins and methods for creating plants, especially plants belonging to the family Rutaceae, with enhanced disease resistance.

SUMMARY OF THE INVENTION

In one aspect, the invention provides an isolated nucleic acid sequence encoding a polypeptide comprising an amino acid sequence set forth in SEQ ID NO: 14-26.

In another aspect, the invention provides a construct comprising a nucleotide sequence set forth in SEQ ID NO: 1-13. In one embodiment, the construct comprises a nucleotide sequence having at least about 75%, 80%, 85%, 90%, 95%, 96%, 97%, 98%, or 99% identity with a nucleotide sequence set forth in SEQ ID NO: 1-13. In one embodiment, a nucleotide sequence is operatively linked to a promoter which functions in plants and said promoter expresses a polypeptide sequence set forth in SEQ ID NO: 14-26. In a further embodiment, the promoter is selected from a CaMV 35S promoter, polyubiquitin promoter, tissue specific promoter, and a tissue preferred promoter. In another embodiment, a plant cell comprises the construct.

In another aspect, the invention provides a method for increasing resistance to *citrus* canker disease in a plant or cell, comprising overexpressing at least one nucleotide sequence set forth in SEQ ID NO: 1-13. In one embodiment, a plant, plant cell, seed, or fruit is produced by the method.

In another aspect, the invention provides a method for increasing resistance to *citrus* canker disease in a plant or cell, comprising (a) transforming a plant or cell with a construct comprising at least one nucleotide sequence set forth in SEQ ID NO: 1-13, operably linked to a promoter active in plant cells; (b) regenerating a plant from said transformed plant or cell; and (c) selecting a plant or cell that has increased resistance to *citrus* canker disease relative to a control plant. In one embodiment, the promoter is operably linked to an enhancer. In another embodiment, the promoter is a constitutive promoter or a tissue-specific promoter. In a further embodiment, the tissue specific promoter is a xylem-specific promoter, phloem-specific promoter, or a xylem/phloem-specific promoter. In another embodiment, the plant is a member of the Rutaceae family. In a further embodiment, the plant is selected from the genera of *Citrus, Poncirus, Fortunella, Murraya, Microcitrus, Limonia*, and *Eremocitrus*. In another embodiment, a plant. In another embodiment, a plant cell, seed, or fruit is produced by the method.

In another aspect, the invention provides a transgenic plant having incorporated into its genome a nucleotide sequence that encodes a disease resistance polypeptide set forth in SEQ ID NO: 14-26. In one embodiment, the polypeptide is encoded by a nucleotide sequence set forth in SEQ ID NO: 1-13. In a further embodiment, progeny, fruit, or seed of the plant comprise said nucleotide sequence.

BRIEF DESCRIPTION OF THE SEQUENCES IN SEQUENCE LISTING

Figure 1:
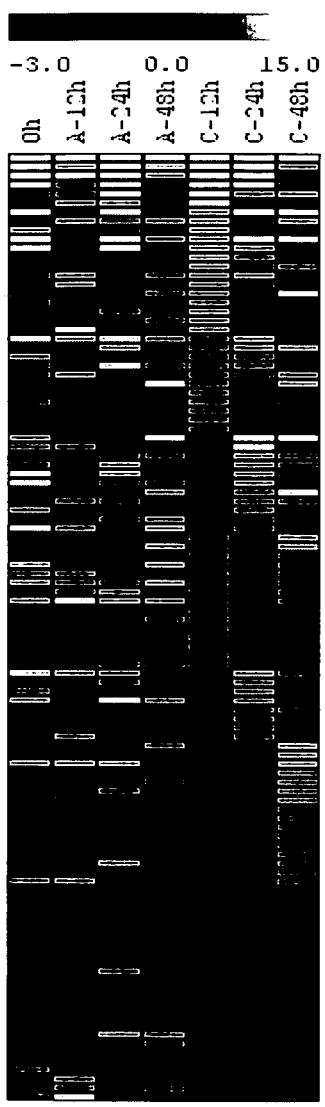
FIG. 1. In silico expression profiles of a selected sample of genes identified in cDNA libraries constructed from *citrus* leaf tissue previously challenged with *Xanthomonas axonopodis* pv *citri* (A-12h, A-24h e A-48h) e *Xanthomonas axonopodis* pv *aurantifolii* (C-12h, C-24h e C-48h).

SEQ ID NO: 1 *Citrus senensis* DNA sequence encoding a polypeptide with similarity to a glycine-rich protein belonging to the shepherin family of antimicrobial peptides.

SEQ ID NO: 2 *Citrus senensis* DNA sequence encoding a polypeptide with similarity to an enzyme of the peroxidase family.

SEQ ID NO: 3 *Citrus senensis* DNA sequence encoding a polypeptide with similarity to an antimicrobial peptide of the snakin family.

SEQ ID NO: 4 *Citrus senensis* DNA sequence encoding a polypeptide with similarity to an enzyme with phosphatase activity.

SEQ ID NO: 5 *Citrus senensis* DNA sequence encoding a polypeptide with similarity to an enzyme with E3 ligase activity.

SEQ ID NO: 6 *Citrus senensis* DNA sequence encoding a polypeptide with similarity to an enzyme with E3 ligase activity.

SEQ ID NO: 7 *Citrus senensis* DNA sequence encoding a polypeptide with similarity to an enzyme with asparagine synthase activity.

SEQ ID NO: 8 *Citrus senensis* DNA sequence encoding a polypeptide that may be involved in the natural defense system of plants.

SEQ ID NO: 9 *Citrus senensis* DNA sequence encoding a polypeptide with similarity to a transcription factor of the Ethylene Responsive Element Binding Protein family.

SEQ ID NO: 10 *Citrus senensis* DNA sequence encoding a polypeptide that may be involved in the natural defense system of plants.

SEQ ID NO: 11 *Citrus senensis* DNA sequence encoding a polypeptide with similarity to a theoretical protein of yet unknown function; however, it has domains similar to those found in transcription factor of the FRIGIDA family.

SEQ ID NO: 12 *Citrus senensis* DNA sequence encoding a polypeptide that may be involved in the natural defense system of plants.

SEQ ID NO: 13 *Citrus senensis* DNA sequence encoding a polypeptide with similarity to an enzyme with transferase activity.

SEQ ID NO: 14 predicted protein sequence for SEQ ID NO: 1.

SEQ ID NO: 15 predicted protein sequence for SEQ ID NO: 2.

SEQ ID NO: 16 predicted protein sequence for SEQ ID NO: 3.

SEQ ID NO: 17 predicted protein sequence for SEQ ID NO: 4.

SEQ ID NO: 18 predicted protein sequence for SEQ ID NO: 5.

SEQ ID NO: 19 predicted protein sequence for SEQ ID NO: 6.

SEQ ID NO: 20 predicted protein sequence for SEQ ID NO: 7.

SEQ ID NO: 21 predicted protein sequence for SEQ ID NO: 8.

SEQ ID NO: 22 predicted protein sequence for SEQ ID NO: 9.

SEQ ID NO: 23 predicted protein sequence for SEQ ID NO: 10.

SEQ ID NO: 24 predicted protein sequence for SEQ ID NO: 11.

SEQ ID NO: 25 predicted protein sequence for SEQ ID NO: 12.

SEQ ID NO: 26 predicted protein sequence for SEQ ID NO: 13.

DETAILED DESCRIPTION OF THE INVENTION

The present invention relates to methods of regulating the natural defense system of plants through the introduction of foreign/native genes into plant cells, preferably into their genomes. More specifically, the methods relate to increasing plant disease resistance by overexpressing genes involved in the innate plant defense system.

The present inventors used expressed sequence tag libraries (EST's), in combination with challenging *citrus* plants with avirulent and virulent bacterial pathogens, to identify genes involved in the effector-dependent hypersensitive reaction (HR) and disease resistance. A total of 2868 putative genes were found to be differentially expressed in *citrus* plants challenged with an avirulent pathogen, as compared to those inoculated with a virulent bacterial strain. Among those, 29 genes were selected to test their individual potential to confer resistance to *citrus* plants against the most common bacterial pathogens of *citrus*.

The inventors found that the overexpression of 13 of these genes conferred enhanced resistance to *citrus* plants against *Xanthomonas axonopodis* pv. *citri*, the causal agent of *citrus* canker disease. These 13 genes, as denoted in SEQ ID NOs: 1-13, are related in that each encodes a protein involved in plant defense.

All technical terms used herein are terms commonly used in biochemistry, molecular biology and agriculture, and can be understood by one of ordinary skill in the art to which this invention belongs. Those technical terms can be found in: Molecular Cloning: A Laboratory Manual, 3rd ed., vol. 1-3, ed. Sambrook and Russel, Cold Spring Harbor Laboratory Press, Cold Spring Harbor, N.Y., 2001; Current Protocols in Molecular Biology, ed. Ausubel et al., Greene Publishing Associates and Wiley-Interscience, New York, 1988 (with periodic updates); SHORT Protocols in Molecular Biology: A Compendium of Methods From Current Protocols in Molecular Biology, $5^{th}$ ed., vol. 1-2, ed. Ausubel et al., John Wiley & Sons, Inc., 2002; Genome Analysis: A Laboratory Manual, vol. 1-2, ed. Green et al., Cold Spring Harbor Laboratory Press, Cold Spring Harbor, N.Y., 1997. Methodology involving plant biology techniques is described herein and is described in detail in treatises such as Methods in Plant Molecular Biology: A Laboratory Course Manual, ed. Maliga et al., Cold Spring Harbor Laboratory Press, Cold Spring Harbor, N.Y., 1995. Various techniques using PCR are described, e.g., in Innis et al., PCR Protocols: A Guide to METHODS AND APPLICATIONS, Academic Press, San Diego, 1990 and in Dieffenbach and Dveksler, PCR PRIMER: A LABORATORY MANUAL, $2^{nd}$ ed., Cold Spring Harbor Laboratory Press, Cold Spring Harbor, N.Y., 2003. PCR-primer pairs can be derived from known sequences by known techniques such as using computer programs intended for that purpose, e.g., Primer, Version 0.5, 1991, Whitehead Institute for Biomedical Research, Cambridge, Mass. Methods for chemical synthesis of nucleic acids are discussed, for example, in Beaucage and Caruthers, *Tetra. Letts.* 22:1859-1862 (1981), and Matteucci and Caruthers, *J. Am. Chem. Soc.* 103:3185 (1981).

Restriction enzyme digestions, phosphorylations, ligations and transformations were done as described in Sambrook et al., MOLECULAR CLONING: A LABORATORY MANUAL, $2^{nd}$ ed. (1989), Cold Spring Harbor Laboratory Press. All reagents and materials used for the growth and maintenance of bacterial cells were obtained from Aldrich Chemicals (Milwaukee, Wis.), DIFCO Laboratories (Detroit, Mich.), Invitrogen (Gaithersburg, Md.), or Sigma Chemical Company (St. Louis, Mo.) unless otherwise specified.

The terms "encoding" and "coding" refer to the process by which a gene, through the mechanisms of transcription and translation, provides information to a cell from which a series of amino acids can be assembled into a specific amino acid sequence to produce an active enzyme. Because of the degeneracy of the genetic code, certain base changes in DNA sequence do not change the amino acid sequence of a protein. It is therefore understood that modifications in a nucleotide sequence encoding any of the proteins of this invention, which do not substantially affect their functional properties, are contemplated.

In this description, "expression" denotes the production of the protein product encoded by a gene. "Overexpression" refers to the production of a gene product in transgenic organisms that exceeds levels of production in normal or non-transformed organisms.

Differentially Expressed Sequences

The differentially expressed genes referred to in this invention have been identified in several *citrus* species, exemplified by sweet orange plants. In the context of the present invention, "deg" refers to a differentially expressed gene whose overexpression confers resistance to plants against plant diseases. Exemplary deg sequences are set forth in "Brief description of the Sequences."

The differentially expressed genes from *Citrus sinensis* will henceforth be called deg 1 (SEQ ID NO: 1), deg 2 (SEQ ID NO: 2), deg 3 (SEQ ID NO: 3), deg 4 (SEQ ID NO: 4), deg 5 (SEQ ID NO: 5), deg 6 (SEQ ID NO: 6), deg 7 (SEQ ID NO: 7), deg 8 (SEQ ID NO: 8), deg 9 (SEQ ID NO: 9), deg 10 (SEQ ID NO: 10), deg 11 (SEQ ID NO: 11), deg 12 (SEQ ID NO: 12), and deg 13 (SEQ ID NO: 13).

The terms "sequence identity" and "sequence similarity" can be determined by alignment of two peptide or two nucleotide sequences using global or local alignment algorithms. Sequences may then be referred to as "substantially identical" or "essentially similar" when they share at least 70% of sequence identity over their entire length, respectively. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or EmbossWin version 2.10.0 (using the program "needle"). Alternatively percent similarity or identity may be determined by searching against databases, using algorithm as FASTA, BLAST, etc.

As noted above, the present invention provides nucleic acid molecules comprising the nucleotide sequences of SEQ ID NO: 1-13, encoding functional proteins, wherein the proteins have amino acid sequences set forth in SEQ ID NO: 14-26. It is understood that the proteins of the invention encompass amino acid substitutions, additions, and deletions that do not alter the function of any of the proteins.

Because many proteins are encoded by gene families, it is expected that other *citrus* genes could have similar functions as those proteins encoded by SEQ ID NO: 1-13. These genes can be identified and functionally annotated by sequence comparison. A worker skilled in the art can identify a functionally related protein sequence with the aid of conventional methods such as screening cDNA libraries or genomic libraries with suitable hybridization probes. The skilled artisan knows that paralogous sequences can also be isolated with the aid of (degenerate) oligonucleotides and PCR-based methods.

Accordingly, the sequences can be identified by the methods described supra, and therefore functionally annotated as belonging to any of the DEG families included in this invention. (Pursuant to common usage, italicization denotes a gene and capitalization an encoded product.) Therefore, the phrase "deg DNA sequence" here refers to any nucleic acid molecule with a nucleotide sequence capable of hybridizing under stringent conditions with any of the sequence set forth in SEQ ID NO: 1-13, and coding for a polypeptide equivalent to the proteins having amino acid sequences set forth as SEQ ID NO: 14-26. The term also includes sequences which cross-hybridize with SEQ ID NO: 1-13, preferably having at least about 75%, 80%, 85%, 90%, 95%, 96%, 97%, 98%, or 99% identity with the genes shown in SEQ ID NO: 1-13. The nucleotide sequences of the invention may encode proteins which are homologous to the predicted gene products disclosed herein as SEQ ID NO: 14-26. The invention also includes a protein sequence that preferably is at least about 75%, 80%, 85%, 90%, 95%, 96%, 97%, 98%, or 99% identical to any of SEQ ID NO: 14-26.

"Stringent conditions" as used herein, refers to parameters with which the art is familiar, such as hybridization in 3.5× SSC, 1×Denhardt's solution, 25 mM sodium phosphate buffer (pH 7.0), 0.5% SDS, and 2 m M EDTA for 18 hours at 65° C., followed by 4 washes of the filter at 65° C. for 20 minutes, in 2×SSC, 0.1% SDS, and a final wash for up to 20 minutes in 0.5×SSC, 0.1% SDS, or 0.3×SSC and 0.1% SDS for greater stringency, and 0.1×SSC, 0.1% SDS for even greater stringency. Other conditions may be substituted, as long as the degree of stringency is equal to that provided herein, using a 0.5×SSC final wash.

Accordingly, the present invention comprises any nucleic acid, gene, polynucleotide, DNA, RNA, mRNA, or cDNA molecule from a *citrus* plant species, or produced synthetically, that increases disease resistance. The DNA or RNA may be double-stranded or single-stranded. Single-stranded DNA may be the coding strand, also known as the sense strand, or it may be the non-coding strand, also called the anti-sense strand.

As used herein, "deg genes as set forth in SEQ ID NO: 1-13" is understood to mean that the deg genes includes the sequences set forth in SEQ ID NO: 1-13, as well as nucleic acid molecules comprised of variants of SEQ ID NO: 1-13, with one or more bases deleted, substituted, inserted, or added, which variant codes for a polypeptide with the same activity. Accordingly, sequences having "base sequences with one or more bases deleted, substituted, inserted, or added" retain physiological activity even when the encoded amino acid sequence has one or more amino acids substituted, deleted, inserted, or added. Due to degeneracy of the genetic code, different nucleotide codons may be used to code for a particular amino acid. A host cell often displays a preferred pattern of codon usage (Campbell et al., 1990). Nucleic acid sequences are preferably constructed to utilize the codon usage pattern of the particular host cell. This generally enhances expression of the nucleic acid sequence in a transformed host cell. The nucleic acid sequences disclosed herein preferably utilize the optimal codon usage for bacterial, fungal and plant host cells. Additionally, multiple forms of the proteins of this invention may exist, which may be due to post-translational modification of a gene product, or to multiple forms of the deg genes. Nucleotide sequences that have such modifications and encode similar proteins are included within the scope of the present invention.

For example, the poly A tail or 5'- or 3'-end, nontranslation regions may be deleted, and bases may be deleted to the extent that amino acids are deleted. Bases may also be substituted, as long as no frame shifts result. Bases also may be "added" to the extent that amino acids are added. It is essential; however, that any such modifications do not result in the loss of the protein activity. A modified DNA in this context can be obtained by modifying the DNA base sequences of the invention so that amino acids at specific sites are substituted, deleted, inserted, or added by site-specific mutagenesis, for example. Zoller & Smith, *Nucleic Acid Res.* 10: 6487-500 (1982).

A deg gene sequence can be synthesized ab initio from the appropriate bases, for example, by using any appropriate protein sequence disclosed herein as a guide to create a DNA molecule that, though different from the native DNA sequence, results in the production of proteins with the same or similar amino acid sequences.

By "isolated" nucleic acid molecule(s) means a nucleic acid molecule, DNA or RNA, which has been removed from its native environment. For example, recombinant DNA molecules contained in a DNA construct are considered isolated for the purposes of the present invention. Further examples of isolated DNA molecules include recombinant DNA molecules maintained in heterologous host cells or DNA molecules that are purified, partially or substantially, in solution. Isolated RNA molecules include in vitro RNA transcripts of the DNA molecules of the present invention. Isolated nucleic acid molecules, according to the present invention, further include such molecules produced synthetically.

"Exogenous nucleic acid" refers to a nucleic acid, DNA or RNA, which has been introduced into a cell (or the cell's ancestor) through the efforts of humans. Such exogenous nucleic acid may be a copy of a sequence which is naturally found in the cell into which it was introduced, or fragments thereof.

In contrast, "endogenous nucleic acid" refers to a nucleic acid, gene, polynucleotide, DNA, RNA, mRNA, or cDNA molecule that is present in the genome of a plant or organism that is to be genetically engineered. An endogenous sequence is "native" to, i.e., indigenous to, the plant or organism that is to be genetically engineered.

"Heterologous nucleic acid" refers to a nucleic acid, DNA or RNA, which has been introduced into a cell (or the cell's ancestor). Such heterologous nucleic acid may comprise segments that are a copy of a sequence which is naturally found in the cell into which it has been introduced, or fragments thereof.

Unless otherwise indicated, all nucleotide sequences determined by sequencing a DNA molecule herein were determined using an automated DNA sequencer, such as the Model 3730 from Applied Biosystems, Inc. Therefore, as is known in the art for any DNA sequence determined by this automated approach, any nucleotide sequence determined herein may contain some errors. Nucleotide sequences determined by automation are typically at least about 95% identical, more typically at least about 96% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence may be completely different from the amino acid sequence actually encoded by the sequenced DNA molecule, beginning at the point of such an insertion or deletion.

A "variant" is a nucleotide or amino acid sequence that deviates from the standard, or given, nucleotide or amino acid sequence of a particular gene or protein. The terms "isoform," "isotype," and "analog" also refer to "variant" forms of a nucleotide or an amino acid sequence. An amino acid sequence that is altered by the addition, removal, or substitution of one or more amino acids, or a change in nucleotide sequence may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software. "Variant" also may refer to a "shuffled gene," such as those described in Maxygen-assigned patents. For instance, a variant of the present invention may include variants of sequences and desired polynucleotides that are modified according to the methods and rationale disclosed in, for example, U.S. Pat. No. 6,132,970.

Methods for Overexpressing Deg Genes

In one aspect of the invention, plant disease resistance is increased by overexpressing a deg gene. Various methods for overexpressing a particular gene are well-known in the art and may be used in the present invention.

The present invention contemplates overexpression of a DEG-encoding sequence. Sense polynucleotides employed in carrying out the present invention are of a length sufficient to express a functional protein in a plant cell. Such polynucleotides may be essentially an entire genomic or complementary nucleic acid encoding any the DEG protein included in this invention.

The suitability of candidate targets also may be evaluated by testing their accessibility to hybridization with complimentary oligonucleotides, using ribonuclease protection assays as are known in the art. DNA encoding enzymatic RNA molecules may be produced in accordance with known techniques. For example, see Cech et al., U.S. Pat. No. 4,987,071; Keene et al., U.S. Pat. No. 5,559,021; Donson et al., U.S. Pat. No. 5,589,367; Torrence et al., U.S. Pat. No. 5,583,032; Joyce, U.S. Pat. No. 5,580,967; Gold et al., U.S. Pat. No. 5,595,877; Wagner et al., U.S. Pat. No. 5,591,601; and U.S. Pat. No. 5,622,854.

For example, deg gene expression may be increased through genetic engineering methods that are well known in the art. Expression can be increased by operably linking a strong promoter sequence to any DEG-encoding sequence included in this invention. Expression may be further increased by adding an enhancer sequence to a strong promoter operably linked to any DEG-encoding sequence included in this invention.

"Enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box. A promoter may naturally comprise one or more enhancer elements that affect the transcription of an operably linked polynucleotide sequence. An isolated enhancer element may also be fused to a promoter to produce a chimeric promoter.cis-element, which confers an aspect of the overall modulation of gene expression. A promoter or promoter fragment may comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention. Several enhancers are known in the art including the 35S CaMV enhancers.

Nucleic Acid Constructs

In accordance with one aspect of the invention, one or more sequences that increase disease resistance are incorporated into a nucleic acid construct that is suitable for plant or cell transformation. The invention provides nucleic acid molecules that increase disease resistance in a transformed plant.

Recombinant nucleic acid constructs may be made using standard techniques. For example, a nucleotide sequence for transcription may be obtained by treating a vector containing said sequence with restriction enzymes to cut out the appropriate segment. The nucleotide sequence for transcription may also be generated by annealing and ligating synthetic oligonucleotides or by using synthetic oligonucleotides in a polymerase chain reaction (PCR) to give suitable restriction sites at each end. The nucleotide sequence then is cloned into a vector containing suitable regulatory elements, such as upstream promoter and downstream terminator sequences.

An important aspect of the present invention is the use of nucleic acid constructs wherein a DEG-encoding sequence is operably linked to one or more regulatory sequences, which drive expression of the sequence in certain cell types, organs, or tissues without unduly affecting normal development or physiology.

"Promoter" connotes a region of DNA upstream from the start of transcription that is involved in recognition and binding of RNA polymerase and other proteins to initiate transcription. A "constitutive promoter" is one that is active throughout the life of the plant and under most environmental conditions. Tissue-specific, tissue-preferred, cell type-specific, and inducible promoters constitute the class of "non-constitutive promoters." "Operably linked" refers to a functional linkage between a promoter and a second sequence, where the promoter sequence initiates and mediates transcription of the DNA sequence corresponding to the second sequence. In general, "operably linked" means that the nucleic acid sequences being linked are contiguous.

Suitable promoters are illustrated by but are not limited to constitutive promoters such as the cauliflower mosaic virus (CaMV) 35S promoter or the polyubiquitin promoter, as well as tissue-specific, tissue-preferred, cell type-specific, and inducible promoters. For example, in *citrus*, several important pathogens are located in the vascular system, which refers to either the xylem or the phloem vessels; it may be advantageous to use a xylem/phloem-specific promoter to target the expression of a defense gene. Xylem or Phloem specific promoters are known in the art, for example, those disclosed in U.S. Pat. No. 6,613,960 and U.S. Application Publication Nos. 2004/0253717 and 2007/0266457.

The vectors of the invention may also contain termination sequences, which are positioned downstream of the nucleic acid molecules of the invention, such that transcription of mRNA is terminated, and polyA sequences added. Exemplary of such terminators are the cauliflower mosaic virus (CaMV) 35S terminator and the nopaline synthase gene (Tnos) terminator. The expression vector also may contain enhancers, introns, start codons, splicing signal sequences, and targeting sequences to cellular organelles such as mitochondria and chloroplasts.

Expression vectors of the invention may also contain a selection marker by which transformed cells can be identified in culture. The marker may be associated with the heterologous nucleic acid molecule, i.e., the gene operably linked to a promoter. As used herein, the term "marker" refers to a gene encoding a trait or a phenotype that permits the selection of, or the screening for, a plant or cell containing the marker. In plants, for example, the marker gene will encode antibiotic or herbicide resistance. This allows for selection of transformed cells from among cells that are not transformed or transfected.

Examples of suitable selectable markers include adenosine deaminase, dihydrofolate reductase, hygromycin-B-phosphotransferase, thymidne kinase, xanthine-guanine phosphoribosyltransferase, glyphosate and glufosinate resistance, and amino-glycoside 3'-O-phosphotranserase (kanamycin, neomycin and G418 resistance). These markers may include resistance to G418, hygromycin, bleomycin, kanamycin, spectinomycin, and gentamicin. The construct may also contain the selectable marker gene ahas that confers resistance to herbicides such as imazethapyr, imazapic, imazapyr, imazamox, sulfometuron methyl, imazaquin, chlorimuron ethyl, metsulfuron methyl, rimsulfuron, thifensulfuron methyl, pyrithiobac sodium, tribenuron methyl, and nicosulfuron [sic: "imidazolinone class"]. Sun-Mi et al., 2004, *Biochemical Journal* 383: 53-61. Other suitable selection markers are known as well.

Visible markers such as green florescent protein (GFP) may be used. Methods for identifying or selecting transformed plants based on the control of cell division have also been described. See WO 2000/052168 and WO 2001/059086.

Replication sequences, of bacterial or viral origin, may also be included to allow the vector to be cloned in a bacterial or phage host. Preferably, a broad host range prokaryotic origin of replication is used. A selectable marker for bacteria may be included to allow selection of bacterial cells bearing the desired construct. Suitable prokaryotic selectable markers also include resistance to antibiotics such as kanamycin or tetracycline.

Other nucleic acid sequences encoding additional functions may also be present in the vector, as is known in the art. For instance, when *Agrobacterium* is the host, T-DNA sequences may be included to facilitate the subsequent transfer to and incorporation into plant chromosomes.

Plants for Genetic Engineering

The present invention comprehends the genetic manipulation of plants, especially *citrus*, to enhance disease resistance.

In this description, "plant" denotes any cellulose-containing plant material that can be genetically manipulated, including but not limited to differentiated or undifferentiated plant cells, protoplasts, whole plants, plant tissues, or plant organs, or any component of a plant such as a leaf, stem, root, bud, tuber, fruit, rhizome, or the like. As used herein, "propagule" includes a structure with the capacity to give rise to a new plant, e.g., a seed, a spore, or a part of the vegetative body capable of independent growth if detached from the parent.

Plants that can be engineered in accordance with the invention include but are not limited to trees, such as sweet oranges, lemons, tangerines, etc. "*Citrus* plant" is understood as meaning a plant of the genera *Citrus, Poncirus, Fortunella, Murraya, Microcitrus, Limonia,* and *Eremocitrus*, preferably the species *Citrus sinensis*.

In the present description, "transgenic plant" refers to a plant that has incorporated a DNA sequence, including but not limited to genes that are not normally present in a host plant genome, DNA sequences not normally transcribed into RNA or translated into a protein ("expressed"), or any other genes or DNA sequences that one desires to introduce into the non-transformed plant, such as genes that normally may be present in the non-transformed plant but that one desires either to genetically engineer or to have altered expression. The "transgenic plant" category includes both a primary transformant and a plant that includes a transformant in its lineage, e.g., by way of standard introgression or another breeding procedure.

"Genetically engineered" (GE) encompasses any methodology for introducing a nucleic acid or specific mutation into a host organism. For example, a *citrus* plant is genetically engineered when it is transformed with a polynucleotide sequence that increases the expression of a gene, such as any deg gene, and thereby increases disease resistance. In contrast, a *citrus* plant that is not transformed with a polynucleotide sequence is a control plant and is referred to as a "non-transformed" plant.

Methods for Genetic Engineering

A polynucleotide sequence, such as a deg sequence, may be stably integrated into a plant genome in various ways known to the art. Monocotyledonous, dicotyledonous angiosperm or gymnosperm plant cells may be transformed For example, see Klein et al., *Biotechnology* 4: 583-590 (1993); Bechtold et al., *C. R. Acad. Sci. Paris* 316:1194-1199 (1993); Bent et al., *Mol. Gen. Genet.* 204:383-396 (1986); Paszowski et al., *EMBO J.* 3: 2717-2722 (1984); Sagi et al., *Plant Cell Rep.* 13: 2615-286 (1994). *Agrobacterium* species such as *A. tumefaciens* and *A. rhizogenes* can be used, for example, in accordance with Nagel et al., *Microbiol Lett* 67: 325 (1990). Additionally, plants may be transformed by *Rhizobium, Sinorhizobium* or *Mesorhizobium* transformation. Broothaerts et al., *Nature* 433:629-633 (2005). See U.S. Application Publication 200702711627.

Additional methods for genetically engineering a plant or cell include, but are not limited to, electroporation, particle gun bombardment (Klein et al. (1987) *Nature.* 327:70-73), calcium phosphate precipitation, and polyethylene glycol fusion, transfer into germinating pollen grains, direct transformation (Lorz et al., *Mol. Genet.* 199: 179-182 (1985)), and other methods known to the art. If a selection marker, such as kanamycin resistance, is employed, it makes it easier to determine which cells have been successfully transformed. Marker genes may be included within pairs of recombination sites recognized by specific recombinases such as cre or flp to facilitate removal of the marker after selection. See U.S. published application No. 2004/0143874.

In the context of the present invention the transgenic plants produced by the method described supra can be used as a source of a transgene in a conventional breeding program. In general, pollen from a transgenic plant is used to pollinate a non-transgenic plant. The seeds of the mother plant can be used to produce a new transgenic plant different from the original transgenic plant produced by the method described supra.

Genetically engineered plants are selected that have increased expression of deg genes. For example, a transgenic *citrus* plant/plant cells employed in the method according to the invention are distinguished from *citrus* wild-type plants/plant cells by the fact that they comprise at least one copy of the nucleic acid molecule set for in SEQ ID NO: 1-13 stably integrated into their genome in addition to copies of such a molecule which occur naturally in the *citrus* wild-type plants/plant cells. In this case, the *citrus* plants/plant cells of the method according to the invention can be distinguished from *citrus* wild-type plants/plant cells in particular by the fact that this additional copy, or these additional copies, is/are located at locations in the genome where it does not occur, or where they do not occur, in *citrus* wild-type plants/plant cells.

"*Citrus* wild-type plant" refers to control plants whose genome is not modified by the introduction of a construct comprising any deg gene sequence, or fragment thereof.

Methods for Quantifying Increased Disease Resistance

Genetically engineered plants and cells of the invention are characterized by an enhanced disease resistance. This is achieved by overexpressing deg genes.

"Disease resistance" or "increased/enhanced disease resistance" refers to an enhanced ability of transformants (compared to wild type or control transformants) to withstand the attack of one or more plant pathogens, or in other words, it refers to a significant reduction in disease symptoms in transformants compared to non-transformed (or empty-vector transformed) controls. Disease resistance or enhanced disease resistance may be determined using a variety of methods. Often disease symptoms are scored visually (either in bioassays or in the field) by assessing the disease symptoms at one or more time points after inoculation or contact with a pathogen. Alternative methods include methods whereby the pathogen is detected and optionally quantified. A transgenic plant may thus show enhanced disease resistance if the amount of pathogen detected in/on the tissue is significantly less compared to controls, or if the pathogen spread is significantly slower than in controls. Ultimately, a significant increase in average yield of transformants (e.g. at least 1%, 2%, 5%, 10% or more) compared to controls, when grown under equivalent disease pressure (preferably in the field) provides an indirect measurement of enhanced disease resistance.

Thus, a plurality of transformed plants expressing DEG proteins (or a constitutively active DEG protein) show enhanced disease resistance if they show a significant reduction of disease symptoms, compared to the untransformed or empty-vector transformed controls. Statistical analysis is required to determine whether significant differences exist. Preferably, one or more disease symptoms are on average at least 2%, 5%, 10%, 15%, 20%, 30%, 40%, 50%, or even 100% lower in DEG transformants than in the control plants. As the disease assay is different for every host-pathogen combination, no specific protocol can be provided, but the skilled person knows how to determine whether transformants show significantly enhanced disease resistance to one or more pathogens. Bioassays as known in the art for each plant-pathogen combination can be used to compare resistance of transgenic plants to suitable controls.

Detailed descriptions of plant pathogens, the disease symptoms caused by them and their life cycles can be found for each plant species. For example, *citrus* pathogens are described in COMPENDIUM OF CITRUS DISEASES, Editors L. W. Timmer, Stephen Michael Garnsey, and J. H. Graham (ISBN 0-89054-248-1, APS Press).

Pathogens of *citrus* include, for example, the following fungal and bacterial species and viruses (non-limiting): *Xanthomonas campestris* pv. *citrumelo* (Bacterium), *Pseudomonas syringae* (Bacterium), *Xanthomonas axonopodis* pv. *citri* (Bacterium), *Xylella fastidiosa* (Bacterium), *Candidatus Liberibacter africanus* (Bacterium), *Candidatus Liberibacter americanus* (Bacterium), *Candidatus Liberibacter asiaticus* (Bacterium), *Alternaria alternata* (Fungus), *Aspergillus flavus, Alternaria alternata* (Fungus), *Alternaria citri* (Fungus), *Glomerella cingulata* (Fungus), *Colletotrichum gloeosporioides* (Fungus), *Thanatephorus cucumeris* (Fungus), *Rhizoctonia solani* (Fungus), *Aspergillus niger* (Fungus), *Thielaviopsis basicola* (Fungus), *Chalara elegans* (Fungus), *Guignardia citricarpa* (Fungus), *Phyllosticta citricarpa* (Fungus), *Penicillium italicum* (Fungus), *Botrytis cinerea* (Fungus), *Botryotinia fuckeliana* (Fungus), *Sphaeropsis tumefaciens* (Fungus), *Phytophthora citricola, P. citrophthora, P. hibernalis, P. nicotianae, P. parasitica, P. palmivora, P. syringae, Macrophomina phaseolina* (Fungus), *Pythium* sp., *P. aphanidermatum, P. debaryanum, P. rostratum, P. ultimum, P. vexans, Rhizoctonia solani* (Fungus), *Lasiodiplodia theobromae* (Fungus), *Botryodiplodia theobromae* (Fungus), *Diplodia natalensis* (Fungus), *Botryosphaeria rhodina* (Fungus), *Botryosphaeria ribis* (Fungus), *Nectria haematococca* (Fungus), *Schizothyrium pomi* (Fungus), *Fusarium oxysporum* (Fungus), *Botrytis cinerea* (Fungus), *Mycosphaerella citri* (Fungus), *Penicillium digitatum* (Fungus), *Ganoderma applanatum* (Fungus), *G. brownii* (Fungus), *G. lucidum* (Fungus), *Mycosphaerella horii* (Fungus), *M. lageniformis* (Fungus), *Phoma tracheiphila* (Fungus), *Alternaria limicola* (Fungus), *Diaporthe citri* (Fungus), *Phomopsis citri* (Fungus), *Mucor paronychia* (Fungus), *M. racemosus* (Fungus), *Armillaria mellea* (Fungus), *Phaeoramularia angolensis* (Fungus), *Phymatotrichopsis omnivora* (Fungus), *Phomopsis citri* (Fungus), *Erythricium salmonicolor* (Fungus), *Gliocladium roseum* (Fungus), *Pleospora herbarum* (Fungus), *Oxyporus latemarginatus* (Fungus), *Poria latemarginata* (Fungus), *Colletotrichum acutatum* (Fungus), *Oidium tingitaninum* (Fungus), *Acrosporium tingitaninum* (Fungus), *Rhizopus stolonifer* (Fungus), *Lasiodiplodia theobromae* (Fungus), *Hendersonula toruloidea* (Fungus), *Elsinoe fawcettii* (Fungus), *Sclerotinia sclerotiorum* (Fungus), *Septoria citri* (Fungus), *Gloeodes pomigena* (Fungus), *Geotrichum citri-aurantii* (Fungus), *Galactomyces citri-aurantii* (Fungus), *G. candidum* (Fungus), *Galactomyces geotrichum* (Fungus), *Elsinoe australis* (Fungus), *Corticium stevensii* (Fungus), *Pellicularia koleroga* (Fungus), *Trichoderma viride* (Fungus), *Rhytidhysteron rufulum* (Fungus), *Ustulina deusta* (Fungus), *Penicillium ulaiense* (Fungus), *Rosellinia necatrix* (Fungus), *R. subiculata* (Fungus), *Citrus mosaic* virus, *Satsuma* dwarf-related virus, *Citrus* leaf rugose virus, *Citrus* yellow mosaic virus, Crinkly leaf virus, *Citrus variegation* virus (CVV), *Satsuma* dwarf virus (SDV), *Citrus* tatter leaf virus, *Citrus tristeza* virus (CTV), *Citrus* sudden death virus (CSDV), *Citrus cachexia* viroid, *Citrus* yellow mottle viroid, *Citrus* yellow ringspot viroid, *Citrus exocortis* viroid (CEVd), *Citru Leprosis* virus (CiLV). Due to the non-specific plant defense, it could be expected that genes are effective against other bacteria pathogens.

It is also an embodiment to generate transgenic plants which express several DEG proteins, preferably under the control of different promoters, such as different tissue-specific promoters.

The disease resistance phenotype can be fine-tuned by expressing a suitable amount of DEG proteins at a suitable time and location. Such fine-tuning may be done by determining the most appropriate promoter for a particular host-pathogen combination and also by selecting transgenic "events" which show the desired expression level. A too low level of DEG proteins or too slow induction of DEG protein production following pathogen attack may be insufficient to enhance disease resistance levels. On the other hand, a too high protein level or expression at times and locations devoid of pathogen attack, may result in agronomically undesired phenotypes, such as lesions in leaves or fruit in the absence of pathogens and yield penalties. However, the skilled person can easily generate plants having enhanced disease resistance, but which at the same time are agronomical acceptable. Optimal deg alleles may be isolated or identified as described, e.g., alleles providing high resistance levels and only a weak HR phenotype.

Transformants expressing desired levels of DEG proteins are selected by e.g. analysing copy number (Southern blot analysis), mRNA transcript levels (e.g. RT-PCR using specific deg primer pairs or flanking primers) or by analysing the presence and level of DEG proteins in various tissues (e.g. SDS-PAGE; ELISA assays, etc). For regulatory reasons, preferably single copy transformants are preferably selected and the sequences flanking the site of insertion of the chimeric gene is analysed, preferably sequenced to characterize the "event." High or moderate DEG-expressing transgenic events are selected for further testing until a high performing elite event with a stable deg transgene is obtained.

Transformants expressing one or more deg genes according to the invention may also comprise other transgenes, such as other genes conferring disease resistance or conferring tolerance to other biotic and/or abiotic stresses. To obtain such plants with "stacked" transgenes, other transgenes may either be introgressed into the DEG transformants, or the DEG transformants may be transformed subsequently with one or more other genes, or alternatively several chimeric genes may be used to transform a plant line or variety. For example, several chimeric genes may be present on a single vector, or may be present on different vectors which are co-transformed. Single events containing one or more deg genes can be bred with other events containing one or more of other deg genes to obtain a stacked event with several deg genes.

In one embodiment the following genes are combined with one or more deg genes according to the invention: known disease resistance genes, especially genes conferring enhanced resistance to necrotophic pathogens, virus resistance genes, insect resistance genes, abiotic stress resistance genes (e.g. drought tolerance, salt tolerance, heat- or cold tolerance, etc.), herbicide resistance genes, and the like. The stacked transformants may thus have an even broader biotic and/or abiotic stress tolerance, to pathogen resistance, insect resistance, nematode resistance, salinity, cold stress, heat stress, water stress, etc. Also, deg silencing approaches may be combined with deg expression approaches in a single plant. For example, deg overexpression in rootstocks or scions may confer or enhance rootstock or scion resistance to soil pathogens, vascular pathogens or leaf pathogens.

It is also possible to introduce or introgress deg genes into a plant breeding line which already has a certain level of disease resistance. For durability of disease resistance in the field, it may be desirable to stack several disease resistance mechanisms in a plant, preferably whereby the resistance sources have different underlying molecular mechanisms.

Whole plants, seeds, cells, tissues and progeny (such as F1 hybrids, F2 seeds/plants, etc.) of any of the transformed plants described above are encompassed herein and can be identified by the presence of the transgene in the DNA, for example by PCR analysis using total genomic DNA as template and using deg specific PCR primer pairs. Also "event specific" PCR diagnostic methods can be developed, where the PCR primers are based on the plant DNA flanking the inserted chimeric gene, see U.S. Pat. No. 6,563,026. Similarly, event specific AFLP fingerprints or RFLP fingerprints may be developed which identify the transgenic plant or any plant, seed, tissue or cells derived there from.

It is understood that the transgenic plants according to the invention preferably do not show non-desired phenotypes, such as yield reduction, enhanced susceptibility to diseases (especially to necrotrophs) or undesired architectural changes (dwarfing, deformations) etc. and that, if such phenotypes are seen in the primary transformants, these can be removed by normal breeding and selection methods (crossing/backcrossing/selfing, etc.). Any of the transgenic plants described herein may be homozygous or hemizygous for the transgene.

Specific examples are presented below of methods for obtaining deg genes as well as methods for introducing the target gene into *citrus* to produce plant transformants. They are meant to be exemplary and not as limitations of the present invention.

EXAMPLE 1

Identification of *Citrus* Deg Genes

Sweet orange plants were inoculated by infiltration with a bacterial suspension of $10^8$ CFU/mL of *Xanthomonas axonopodis* pv *citri*, causal agent of *citrus* canker disease. In a parallel experiment, leaves of the same variety were inoculated with a bacterial suspension of $10^8$ CFU/mL of *Xanthomonas axonopodis* pv *aurantifolii* known to elicit a HR in sweet orange plants. A total of four cDNA libraries were constructed from leaf tissue at 0, 12, 24 and 48 hours after the exposure to those bacterial strains. A total of 3000 sequences were produced for each library and clusters were assembled using the CAP3 software (Huang, X. and Madan, A. (1999) CAP3: A DNA sequence assembly program. *Genome Res.*, 9, 868-877). The putative identity of each cluster sequence was determined by comparison with public databases using the BLAST algorithm (Altschul et al., 1997, Nucleic Acid Res. 25:3389-3402).

Differential expression was determined by calculating the relative abundance of ESTs of a particular cluster in each of the constructed libraries (Steckel and Falciani, 2000, Genome Research 10:2055-2061). The probability that this differential expression was not caused by a random event was confirmed by statistical tests (Steckel and Falciani, 2000, Genome Research 10:2055-2061).

Figure 2:
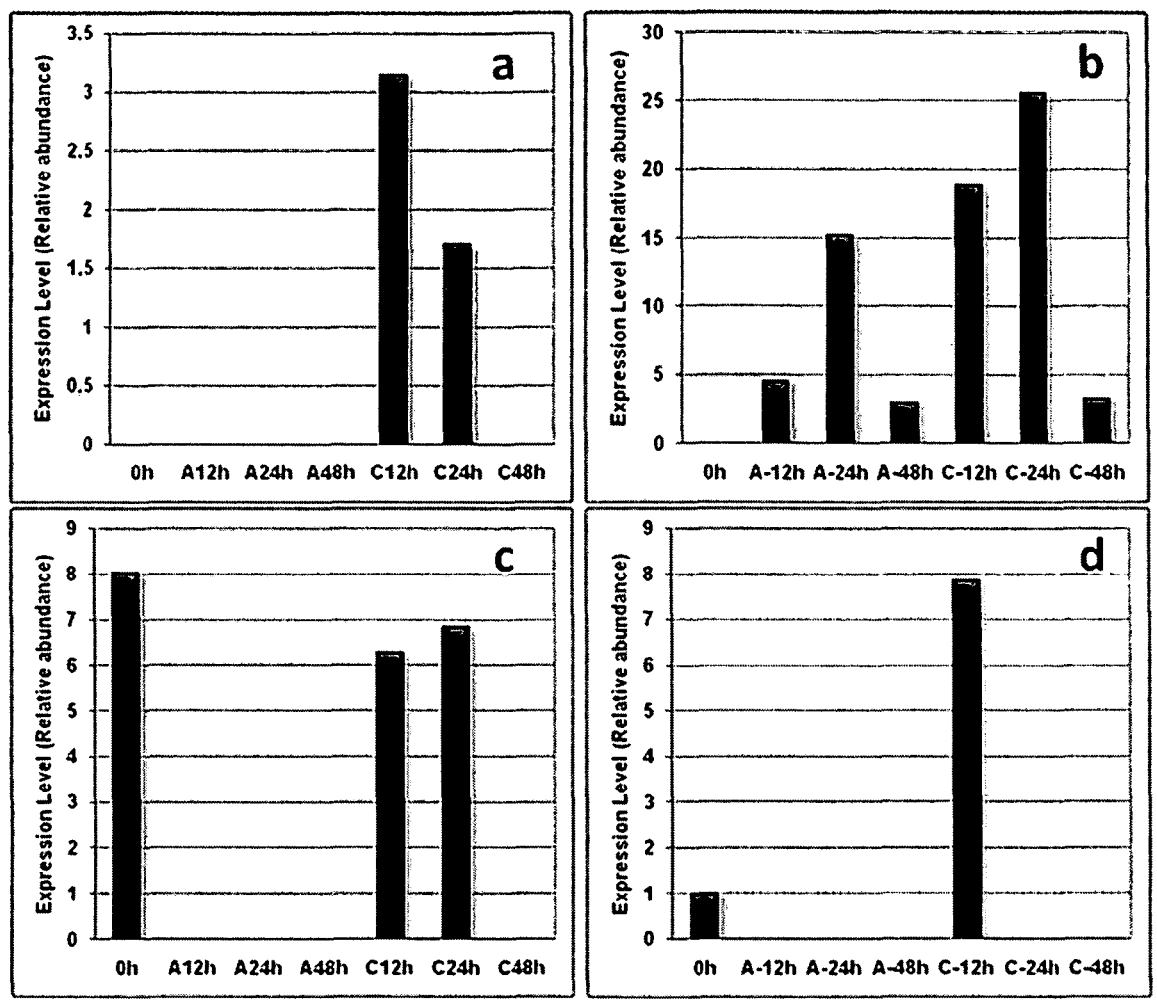
FIG. 2. Differential expression of selected deg genes in *citrus* plants challenged with *Xanthomonas axonopodis* pv citri (A-12, A-24 e A-48) e *Xanthomonas axonopodis* pv *aurantifolii* (C-12h, C-24h e C-48h).

Comparison of the expression profiles of a large number of genes identified in this study indicated that, under disease resistance conditions (HR), several genes exhibited significantly higher levels of expression as compared to diseased tissue (FIG. 1). Among them, a total of 13 genes (SEQ ID NO: 1-13) were chosen as potential candidates to confer disease resistance in *citrus* plants (FIG. 2).

EXAMPLE 2

Vector Construction

Figure 3:
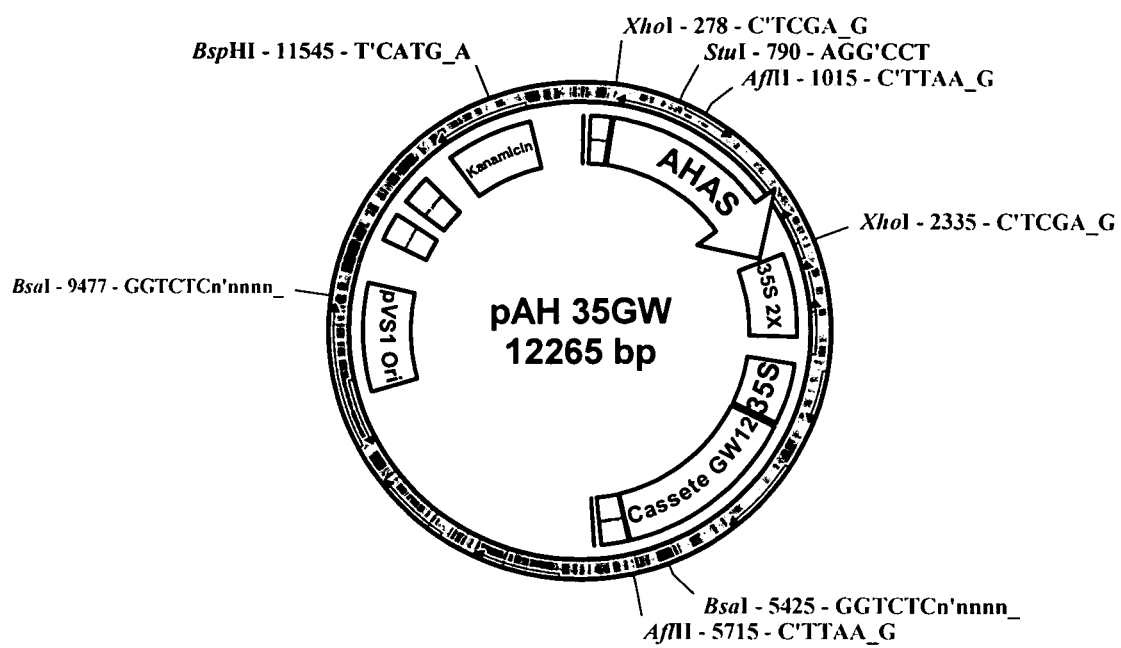
FIG. 3. Schematic representation of pr35S(2x)-CaMV::ahas::35SpolyA|pr35S-CaMV::deg::NOSpolyA vectors.

The ORF (open reading frame) of each candidate gene (SEQ ID NO: 1-13) was PCR amplified using specific primers for the 5' end and 3' end of each gene. Each primer sequence was modified to include the specific sequences required by the GATEWAY™ cloning system (Invitrogen). The amplification products were first cloned into the vector pENTR/TEV/D-TOPO® (Invitrogen) by recombination and their sequence was confirmed by re-sequencing the whole insert. After confirmation of the sequence, the candidate genes were transferred to plasmid pAH35GW by recombination resulting in the generic construct pr35S(2x)-CaMV::ahas::35SpolyA|pr35S-CaMV::deg::NOSpolyA (FIG. 3). The sequence of the resulting constructs was confirmed by re-sequencing the entire TDNA region. Fully validated vectors were used for *citrus* transformation.

EXAMPLE 3

*Citrus* Transformation

Seeds of sweet orange plants cv. Pineapple were germinated in the absence of light for 30 days. Epicotyls of etiolated seedling were cut and infected with *Agrobacterium tumefaciens* carrying each of the candidate genes (SEQ ID NO: 1-13) in a construct. Approximately 40 days after transformation, regenerated plants were individualized and top-grafted onto rootstock seedlings. Grafted plants remained under laboratory conditions for about 2 months when they were transferred to greenhouse conditions. Before initiating the acclimation period, plants were grafted again onto well-developed rootstock plants grown under greenhouse conditions. Acclimation and development of the scion was allowed to last 70 days after which period they were transferred to mother plant blocks.

EXAMPLE 4

Figure 4:
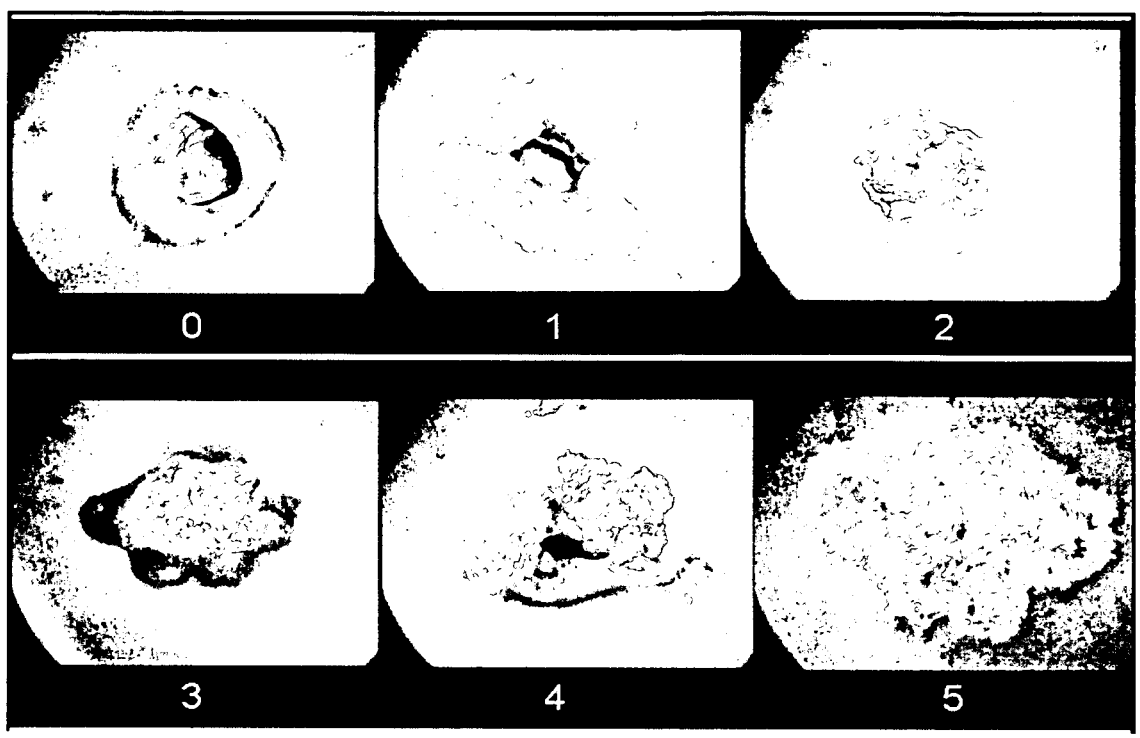
FIG. 4. Diagrammatic scale illustrating the development of *citrus* canker lesions on sweet orange leaves artificially inoculated with a bacterial suspension of *Xanthomonas axonopodis* pv *citri*.
Figure 5:
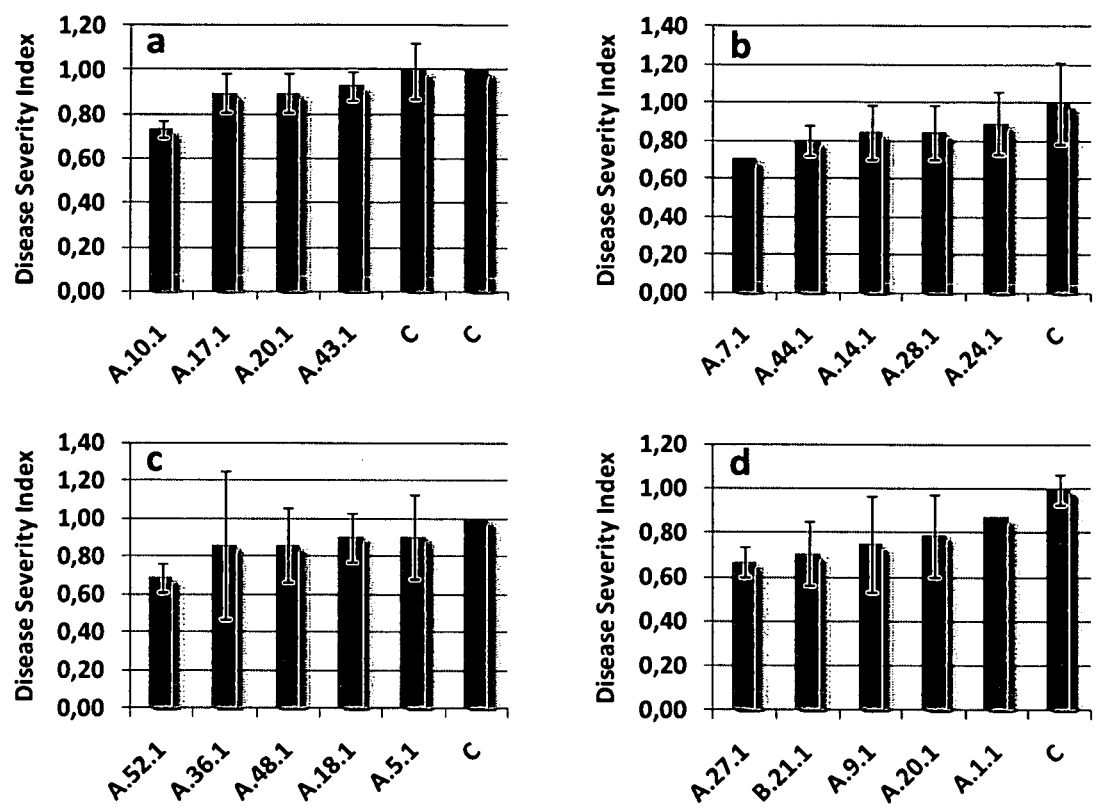
FIG. 5. Disease severity in selected pr35S-CaMV::deg::NOSpolyA events and control variety Pineapple (C).
Figure 6:
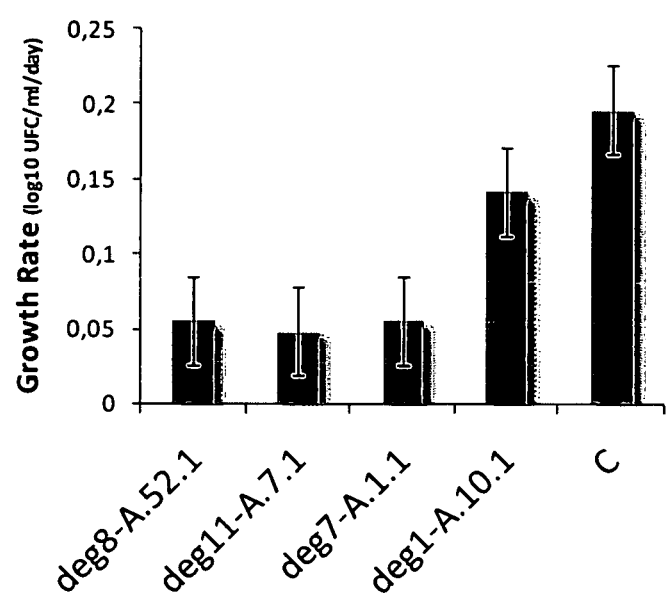
FIG. 6. Differential growth rate of the *citrus* canker bacterium in *citrus* plants carrying the pr35S-CaMV::deg::NOSpolyA constructs and control variety Pineapple (C).
Figure 7:
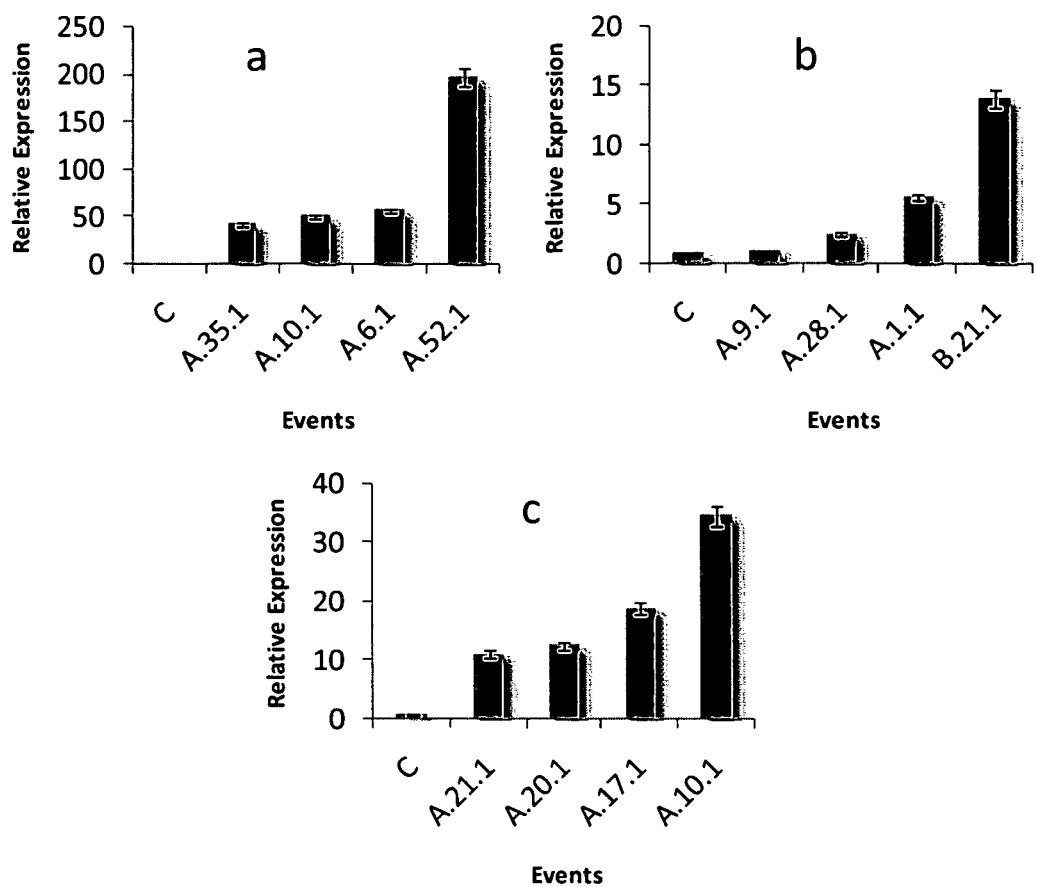
FIG. 7. Transgene expression levels in selected events carrying the pr35S-CaMV::deg::NOSpolyA constructs and control variety Pineapple (C).

Enhanced Disease Resistance in *Citrus* Plants Carrying the pr35S-CaMV::deg::NOSpolyA Constructs To assess the effect of increasing expression of deg genes in transgenic *citrus* plants, a total of 5 leaves were detached from each of 25 independent transgenic events for each of the constructs transformed into *citrus* plants and 3 non-transgenic wild type plants of the sweet orange variety "Pineapple." In summary, each leaf was perforated 6 times using a needle and each hole was immediately put in contact with 5 µl of a bacterial suspension of $10^6$ CFU/ml. Inoculated leaves were incubated in individual humidity chambers and evaluated daily for 15 days. Canker lesions were scored using a proprietary diagrammatic scale (FIG. 4). Analysis of variance (ANOVA) and Dunnett's test for mean comparison for all measurements were performed with the R software package version 2.6.2.

During the course of the experiments, several pr35S-CaMV::deg::NOSpolyA events exhibited a reduced canker development as compared to control leaves. After 15 days incubation, the results indicated that some of the transgenic events exhibited a significant reduction on the severity of the canker symptoms as compared to control plants (FIG. 5). All together, overexpression of deg genes appear to cause, at various degrees, changes in the plant defense system that lead to increased disease resistance.

EXAMPLE 5

Differential Growth Rate of the *Citrus* Canker Bacterium in *Citrus* Plants Carrying the pr35S-CaMV::deg::NOSpolyA Constructs In order to determine the direct effect of the expression of deg genes in transgenic *citrus* plants on the growth of pathogenic bacterial populations, a total of 3 leaves were detached from the best transgenic events identified by the in vitro assay described before and from 3 non-transgenic wild type plants of the sweet orange variety "Pineapple." In summary, each leaf was perforated 6 times using a needle and each hole was immediately put in contact with 5 μl of a bacterial suspension of $10^5$ CFU/ml. Inoculated leaves were incubated in individual humidity chambers and evaluated 0 and 5 days after inoculation. For each evaluation, 3 leaf discs of about 1 $cm^2$ were cut directly from 3 inoculation sites. Each individual discs was ground in liquid nitrogen and used for total DNA extraction using the Wizard® Genomic DNA Purification Kit (Promega). DNA from each individual extraction was used for bacterial enumeration using qPCR (Cubero & Graham, 2005, Phytopathology 95: 1333-1340). Bacterial growth rate was calculated by comparing bacterial populations at 0 and 5 days after de inoculation. Analysis of variance (ANOVA) and Dunnett's test for mean comparison for all measurements were performed with the R software package version 2.6.2.

The results indicated a significant reduction in the growth rate of the *citrus* canker bacterium when deg genes were overexpressed in *citrus* tissue (FIG. 6). These results also confirmed the observations made for the same events regarding the significant reduction of the severity of the disease (FIGS. 5 and 6).

EXAMPLE 6

Transgene Expression Levels in Selected Events Carrying the pr35S-CaMV::deg::NOSpolyA Constructs In order to examine the correlation between the level of expression of transgenes and the response of different events to the *citrus* canker pathogen, a group of transgenic events was selected for the quantification of transcript levels using qRT-PCR. In summary, total RNA was extracted from young *citrus* leaves using the SV Total RNA Isolation System (Promega, Madison, Wis.) according to the manufacturer's instructions. First-strand cDNA was generated by reverse transcription of 1 μg total RNA per sample with Oligo-dT primer using the ImProm-II™ Reverse Transcriptase System (Promega) according to the manufacturer's instructions in a final reaction volume of 20 μL. For RT-PCR, 5 μL of cDNA was added to 12.5 μl, of SYBR® Green Master Mix (Applied Biosystems, Foster City, Calif.) according to the manufacturer's instructions to achieve a final reaction volume of 25 μL RT-PCR was performed using an ABI PRISM® 7000 System (Applied Biosystems). The PCR protocol consisted of: initiation at 1 cycle at 50° C. for 2 min and 1 cycle at 95° C. for 10 min, followed by amplification for 45 cycles at 95° C. for 15 sec and 60° C. for 1 min. Ct data were collected via ABI PRISM® 7000 Sequence Detection System (Applied Biosystems). Each leaf sample was assayed for each gene a minimum of two separate times.

The results indicated a significant variation in the expression level of the transgenes among selected events. However, a significant correlation was observed between the expression level of a given transgene (FIG. 7) and the ability of the corresponding event to limit the growth rate of the bacterium (FIG. 6) which, consequently, reduced the severity of the canker lesions (FIG. 5).

What is claimed is:

1. An isolated cDNA sequence encoding a polypeptide selected from the group consisting of the sequences set forth in SEQ ID NO: 14-26, wherein said cDNA is operably linked to a heterologous promoter.

2. A construct comprising a cDNA sequence selected from the group consisting of the sequences set forth in SEQ ID NO: 1-13, wherein said cDNA sequence encodes a polypeptide selected from the group consisting of the sequences set forth in SEQ ID NO: 14-26 and said cDNA is operably linked to a heterologous promoter.

3. The construct of claim 2, wherein said heterologous promoter functions in plants and said heterologous promoter expresses a polypeptide sequence selected from the group consisting of the sequences set forth in SEQ ID NO: 14-26.

4. The construct of claim 3, wherein the heterologous promoter is selected from the group consisting of a CaMV 35S promoter, polyubiquitin promoter, tissue specific promoter, and a tissue preferred promoter.

5. A plant cell comprising the construct of claim 2.

6. A method for increasing resistance to *citrus* canker disease in a plant or cell, comprising overexpressing at least one cDNA sequence selected from the group consisting of the sequences set forth in SEQ ID NO: 1-13, wherein said cDNA sequence is operably linked to a heterologous promoter.

7. A method for increasing resistance to *citrus* canker disease in a plant or cell, comprising (a) transforming a plant or cell with a construct comprising at least one cDNA sequence set selected from the group consisting of the sequences forth in SEQ ID NO: 1-13, operably linked to a heterologous promoter active in plant cells;

(b) regenerating a plant from said transformed plant or cell; and (c) selecting a plant or cell that has increased resistance to *citrus* canker disease relative to a control plant.

8. The method of claim 7, wherein the promoter is a constitutive promoter or a tissues specific promoter.

9. The method of claim 8, wherein the tissue specific promoter is a xylem-specific promoter, phloem-specific promoter, or a xylem/phloem-specific promoter.

10. The method of claim 7, wherein the promoter is operably linked to an enhancer.

11. The method of claim 7, wherein the plant is a member of the Rutaceae family.

12. The method of claim 11, wherein said plant is selected from the genera of *Citrus, Poncirus, Fortunella, Murraya, Microcitrus, Limonia*, and *Eremocitrus*.

13. A transgenic plant, plant cell, seed, or fruit produced by the method of claim 6 or 7.

14. A transgenic plant having incorporated into its genome a cDNA sequence that encodes a disease resistance polypeptide selected from the group consisting of the sequences set forth in SEQ ID NO: 14-26.

15. The transgenic plant of claim 14, wherein the polypeptide is encoded by a cDNA sequence selected from the group consisting of the sequences set forth in SEQ ID NO: 1-13.

16. A transgenic progeny, fruit, or seed of the plant of claim 15, comprising said cDNA sequence.

17. A construct comprising a cDNA sequence selected from the group consisting of the sequences set forth in SEQ ID NO: 1-13, wherein said sequence is operatively linked to a heterologous promoter which functions in plants and said heterologous promoter expresses a polypeptide sequence selected from the group consisting of the sequences set forth in SEQ ID NO: 14-26.

* * * * *

SEQUENCE LISTING

<160> NUMBER OF SEQ ID NOS: 27

<210> SEQ ID NO 1
<211> LENGTH: 378
<212> TYPE: DNA
<213> ORGANISM: Citrus sinensis

<400> SEQUENCE: 1
atgggttcca aattgttcct tcttttaggc cttttaatgg ccattgctct tcttatctct 60
tccgaggtag cagccagaga cctggccgag acttccattg atcacaacga aaaggctgat 120
aaggccacag agacacatga aattgaggac ggtcgcggcg gatacggcgg cggtggtggg 180
ggctatggcg gtggtggggg ctatggcggt ggtgggggcc atggcggggg ccatggtggt 240
ggccatggcg gtggccatgg cggtggccac tgcccctacg gttgctgtgg acgtggttat 300
tatggaagag gctgcaggtg ctgcacttac gctggtgagg ctgttgatac tgagcctgaa 360

```
accgagcctc aaaactga                                               378
```

```
<210> SEQ ID NO 2
<211> LENGTH: 1008
<212> TYPE: DNA
<213> ORGANISM: Citrus sinensis

<400> SEQUENCE: 2
atgggtacga aagctgtctt cttgctttta gctttgcttt ccttctcagc tgtgtctctg    60
aggtctgctt tggcagaaaa tgaagaggac ccaggtcttg ttatgaattt ttacaaggat   120
acatgccctc aggccgagga cattatcaag gaacaagtta agcttctgta caagcgccac   180
aagaacactg cattttcttg gcttagaaac attttccatg actgtgctgt ccagtcttgt   240
gatgcttcac tgcttctgga ctcgacaaga aagaccttgt ctgagaagga aatggacagg   300
agctttggta tgaggaactt caggtacatt gagaacatca agaagctgt tgaaagagag    360 tgccctggtg ttgtttcctg tgctgatatt cttgtcctgt ccggtagaga tggcgttgtt   420
gcgcttggag gcccttacat tcctctcaag acaggaagaa gagatggtag aaaaagcaga   480
gcagagatac ttgagcagta tctcccagat cacaatgaca gcatgtctgt tgttcttgag   540
aggtttgcag ccattggcat tgacgcccct ggacttgttg ctctgctagg atctcacagt   600
gttggcagaa ctcattgtgt gaagctggtg caccgtctgt acccagaagt tgaccctgca   660
ctgaaccctg accacgttcc gcatatgctc cataagtgtc ctgatgcaat cccagacccc   720
aaggctgttc agtatgtgag gaatgaccgt ggcacaccca tggtgctgga caacaactac   780
tataggaaca tattggacag caagggcttg atgatggttg atcatcagct agccaccgac   840
aagaggacaa gaccttatgt taagaagatg gccaagagtc aagactactt cttcaaggaa   900
ttttcaagag ccattactat cctttctgag aacaaccctc tcaccggtac aaagggtgag   960
atcagaaagg tttgcaatct tgccaacaag ctccacgaca agtcctag             1008

<210> SEQ ID NO 3
<211> LENGTH: 267
<212> TYPE: DNA
<213> ORGANISM: Citrus sinensis

<400> SEQUENCE: 3
atgaagctgg ccttagttac gttccttctc gtttcgcttg tcctcacctc cactttcttt    60
gaggtctcaa tggctggttc agatttctgc gactcaaagt gtgcggtgag gtgctcaaaa   120
gcaggaaggg aagacaggtg cctgaagtac tgtggaattt gctgtgacaa gtgccattgt   180
gttccatctg ggacttacgg gcacaaggac gagtgcccct gctacaggga cctcaagaac   240
tccaagggca aacctaagtg tccttaa                                       267

<210> SEQ ID NO 4
<211> LENGTH: 1080
<212> TYPE: DNA
<213> ORGANISM: Citrus sinensis

<400> SEQUENCE: 4
atggactcag catcgtcagc aacagctgct gctgcaattt ttaatgagag agagtcaatg    60
gtggatccat ttttggttga ggctctccag aatcctcgtc atcgtctcac cattctgcgt   120
atggaacttg atattcagag gtttttgcaa aatcctgatc agcagcattt cgagttccaa   180 catttttccta cttcttatct ccgactggct gcacaccgtg tttctcaaca ttatgggcta   240
gtaactatgg ttcaggaaaa tggcatagaa gggctgggta acaggatttt ggtgaggaaa   300
```

| | |
|---|---|
| acagcagaaa gcaaatatcc tgctgtccgt ttatctgaga ttcctgctaa gcagtcggaa | 360 |
| gaaagtgata agcttgaaaa gattaaaatt gccatcaggc gtaggcccaa tgctggatgt | 420 |
| gttaatggag caaatgaaac tgggacgaaa cgaagtcctg ttagaagtgt ggaagagagg | 480 |
| aaggaggagt atgatcgagc acgtgcccgc atctttagtg gtcctagcag tcctaactca | 540 |
| gaggatacgc ttactcaggt ctctacagat atgaaaaata ttggctttaa ccgagatgag | 600 |
| agggaaattg tcaggaactc cattactgat gcagaaaaga ttattagtat cagagacggt | 660 |
| gctggtttgt ctcgagttgc cattttcaga gacagggaga aggatcgtac tgatccagat | 720 |
| tatgatcgga gttatgaaag gtatgtcagg agccttccaa ctaatcaagg ctttagcttg | 780 |
| ccacctttta atatgcagaa agttcaactt ccatttatgc agtacgatac tggttttccc | 840 |
| caattcagtc agatcccaag gactcaagct tccctcagtt tcaggcctcc gtcaagccca | 900 |
| gttatgagcc cttattgtgc agtgggaccg aatcagacat ctgtggaagc tgcatatatg | 960 |
| caatggccaa gtgctgcaat gatgtatgct cattcgtatg agcagtttag acaagctgct | 1020 |
| ttccaggttc cattctgtca gcaacctctg agctttgatt actctcaaaa ccactcatag | 1080 |

<210> SEQ ID NO 5
<211> LENGTH: 1014
<212> TYPE: DNA
<213> ORGANISM: Citrus sinensis

<400> SEQUENCE: 5

| | |
|---|---|
| atgggcaatt cggagaaaga ttcgacgtcg aagtcaatta cgagacggt gaacgggtcc | 60 |
| caccagttca cggtaaaagg ttactccctg gcgaagggaa tgggccctgg caagtgctta | 120 |
| tcgagcgacg tttttaccgt gggcggttac gattgggcga tttacttta ccccgacggc | 180 |
| aagaacccgg aagatggggc tttgtatgtt tcggtgttta ttgcgttggc gagtgaagga | 240 |
| acggacgtga gggcgctgtt tgagttaact ttggttgacc aaagtgggaa aggaaagcat | 300 |
| aaagttcata gtcattttga tcgagcgtta gagagtggcc cgtacacctt gaagtatcgt | 360 |
| ggaagcatgt ggggctataa cgcttctttt aaaagaacat ctctggagac ttctgattat | 420 |
| attaaggatg attgtcttct catcaactgc actgttggag ttgttagaaa ccgccttgag | 480 |
| ggaccaaaac agtattccat accagtgcca ccgtcagaca tgggccaggg tcttaaggat | 540 |
| ttgctagagt ctgaaattgg atgtgacata gtttttgagg ttggtgatga acatttaaa | 600 |
| gctcataaac tgatacttgc tgctcgctct cctgttttca gagcccaatt ctatgggctt | 660 |
| gttggagatc gtaacttgga taagtagtt gtgaaggatg ttgaaccctc aatcttcaag | 720 |
| gcaatgctcc tgtttatata caccgataaa tttcctgatg tatatgaaat tactggcaca | 780 |
| acatcaatgt gcacaacaac caacatggta cagcatctac tggctgcagc tgatctttat | 840 |
| aatgtagatc gattgaaatt gttgtgtgaa tcaaaattat gtgaagaact aaatgctgag | 900 |
| acagtggcca aaacactcgc actggcagaa caacatcagt gtcccagct taaggctatc | 960 |
| tgcttgaagt ttgctgcaac tccggcgaat ttgggaggtg cgtgttgttc gtag | 1014 |

<210> SEQ ID NO 6
<211> LENGTH: 1029
<212> TYPE: DNA
<213> ORGANISM: Citrus sinensis

<400> SEQUENCE: 6

| | |
|---|---|
| atgaaaatgg aatcttccga gttaataccg agtctccctg aagagctcag cctcgagtgc | 60 |

```
ttaacccgcc tcccttactc cacccatcgc ctcgcctccg ctgtctgccg gcgttggcgc    120
caactccttc aaagccaaga cttttactac caaagaaaaa attctgggca cacccacaaa    180
gttgcgtgct tagttcaagc tgaaaaagaa tcagacggtg gcaaaaaacc aggcgagtca    240
ccgagttatc gactcagcgt gttcgaccgg gtcggtgcgg tatgggacag gattgacccg    300
gtacccgggt atccaaatgg gttgccgctc ttttgtcagt tggcgggttg caagggcaag    360
cttgtggtga tgggcgggtg ggacccggat agttacaacc cggtcaccga cgttttcgtg    420
tacgatttcg ggatgcggag gtggcggaaa gggaaggatt tgccggcgaa gatgtcgttt    480
ttcgggtgtg gatctgcgga gggtcgggtc tatgttgcgg gcgggcacga tcagaataag    540
aacgcgctga ggacggggtg ggtctatgat ttgaggcggg acgagtggag tgagttgact    600
cagttgagtc aagagcgaga cgaatgtgag ggggtggtga taggggatga gttttgggta    660
attagcgggt ataacaccga gaatcaaggg gctttcgatg gaagcgccga cgcttacggg    720
ttcggatccg gtcaatggaa gcgggtggaa gggatttggg aggctggtcg gtgcccgaga    780
tccaacgttg gggtgggcaa agatgggagg atatttagtt ggtccgagct agactccgtt    840
gtacgggccg ggttatgcgg ggtagcgttg ggcgatcggg ttctggtcac cgggtcggag    900
taccaaggag ctccaagtgg gttttatctg gcggaaattg gggaagggca aaaggtgaaa    960
ttggagaaaa tcaatgtgcc cgatgaattt tctgggtttg ttcaatctgg ttgctgcgtt   1020
gagatctaa                                                           1029

<210> SEQ ID NO 7
<211> LENGTH: 690
<212> TYPE: DNA
<213> ORGANISM: Citrus sinensis

<400> SEQUENCE: 7
atgttgggag tgttcagcag cgcgatcgtt tcacctccag aggagctggt ggcggccgga     60
agccggactc cgtcgccgaa gaccacatcg acggcactgg tcgaccgttt cctccaggcc    120
aactcgtctg ctgtgtccgt acaggtcggg gacaacgtca ccctcgcgta cactcatcag    180
aacgagtctc ctttacggca aagatcattt gctgtgaaag atgagatctt ctgcttgttt    240
gagggagcac ttgataactt gggaagcctg aggcagcaat atggactagc taagtcggca    300
aatgaagtga tcttggtgat tgaggcatac aaggctctgc gtgatcgggc ccttacccca    360
ccgaaccatg tcgttggcca ccttagtggg tactttgcct tcattgtcta cgacaagtcc    420
acctccacct tgtttgtggc ttctgaccaa tttggtaagg ttcctctttta ttggggaatc    480 actgctgatg gacatgttgc ctttgctgat gatgctgact tgctcaaagg tgcttgcggc    540
aagtcacttg cttctttccc tcaaggttgt ttcttctcaa cagcagttgg aggactgaga    600
agctttgaga atcaaagaa caagatcact gcagttcctg ctgcggaaga agagatctgg    660
ggtgctacat ttaaggtaat gtcatcttga                                     690

<210> SEQ ID NO 8
<211> LENGTH: 486
<212> TYPE: DNA
<213> ORGANISM: Citrus sinensis

<400> SEQUENCE: 8
atgaaccgct gcgccgttat gggattggga ggaggctgtg atgaagagag gaggatgggt     60
tcaatgattt gccctaagcc aaggagatta ggcctcataa atcctccgat taacgattcc    120
attagacatt tgaaaaggcc agctagtgag tttggagatt caaaagctgg gactgaactt    180
```

```
ctggatttaa ttctcaccaa gggaggctac ggtacagaaa agactggcaa ccaagtggcg      240
tcgtcgccac cttatttctc cggatctcca ccatcgaggg cttcaaatcc tctaatacag      300
gatgcccaat tcggcaatga gaagtcagcc ccgctcactg cagcaccgcc atctccgtcc      360
tcgcggatgg gaggcggcgg atgcgtgagg gtgaaattcg ggcacaagcc tgctgcggtg      420
agaattgaag ggtttgattg tctcagccga gatcgccgca attgcagcat ctctgctgtg      480
gcttaa                                                                 486

<210> SEQ ID NO 9
<211> LENGTH: 762
<212> TYPE: DNA
<213> ORGANISM: Citrus sinensis

<400> SEQUENCE: 9
atgtgtggcg gtgcacttat tgctgattat gatgaagtcc ggccggtcag gcgcgagcgc       60
aaattgacct ccgaggatct ctggtccgag tttggttcca tttccgacct cttgggcttg      120
gactacaatg gcaaatccca ccctaagcaa cctctcaaag tgaaaaatga aaggctgaa       180 gattcaagca ataaagctgc tcgtgttgag gggaaggaga agaagactca gcgagttcgc      240
aagaacgtgt acagaggaat acggcagagg ccgtggggaa aatgggcagc tgaaattaga      300
gacccttaca agggcgtccg cgtttggctc ggcactttca acacagccga agaagccgca      360
agagcttatg atgaagccgc caagcgtatc cgcggcgaca aggccaagct caacttcgct      420
cagccgccgc cgccaatagc tccaccccca gctaagaaac gctgcatgcc atccctgag      480 ttgactcagc cgagatttga aaccatcgga accccaccgg ctccggcgcc gtcccgtgg       540 gtggggtttg ggtatcagaa tgagttttat caacccaggg cagtagacga cgagtttgag      600
ctgagccagc aaatttcgag cttggaatcg ttttttggat tggagccatt aatgagtcag      660
ccgagtggaa acggtgctgg tgggtatgac tcggtggact tttggatgct tgatgacgtg      720
gcggcgactc agcagctgaa cagcaatcag ttcttgtgtt ag                         762

<210> SEQ ID NO 10
<211> LENGTH: 747
<212> TYPE: DNA
<213> ORGANISM: Citrus sinensis

<400> SEQUENCE: 10
atgcaactct caacaaactt cacagcttca ccatttcgat cccaaaacca tctcttcaac       60
aatctcagtc ccacttcttt tctccacaaa tcactgttcc tttcaagacc caccaaaacc      120
ctccaaaatc tgctcttttc aaaccccaaa tcatcacaaa aaagttact tagaacttca      180 acaattaatg cctctttgct tgaagctcca ctcttgtggg ctggtagact ttgcgtttac      240
tatgccctct tgaaagctgg cttagctgga tctcaagcta atcctctcgt tctgatttg       300 gaaagtggtg gtgtcactgg tagtgaaggt gctgatttgg ggttctctaa atggttagaa      360
aacataaaag ggaagccaga caaggaagcg gctgacaaaa ggaaattggt gagcaaatgg      420
catcctacaa caaagggaac actgagacga aattacaggg tgccctccaa atctgaaggg      480
cgcagacttc ttaaagccat tgcgtcgttg ctgtctgatg atgatcactt cacggatgcc      540 acttccccaca agggttgtca aattaggagg gagaatgttc acggtgaatc tgtctgctgc      600
aataacgtta gggctctctt tgatgagctt ccaactcctc acttggttgt ggaaatcaca      660
ccttttccag ccggacctct aaccgaaaag gattacgtca aggctgagaa actagagagg      720
```

```
gtactgaggt cgggcccttc tatttga                                         747
```

<210> SEQ ID NO 11
<211> LENGTH: 1650
<212> TYPE: DNA
<213> ORGANISM: Citrus sinensis

<400> SEQUENCE: 11

```
atggaagaaa accaatcagt tgctacactc atggactcta caacatccaa gattcaacaa      60
cttcagaaag catttgctga acttgaaagt cacagggcca taccccttaa tttgagatgg     120
aaggaacttg aagaacactt ccatgggctt gagaagtcct taaagcgaag gtttcatgaa     180
ctggaagacc aagaaaagga gtttgaaact aaaacaagga agcccgtga atcttgcag      240
aagcgggagg ctgctgtttt ggccaaggaa caaactactc tggagaagct ccagaagaag     300
agagatgctg ctgtctttgc catttcaact gctctagaga acagaggaa ggtatcatct      360
gcagagcctg ccattgttag caatgttgat gaaagcaggg caccacctgt tgaggacaaa     420
ctgcctgatt caatgtctct tgaaaataac ttagaaagca gcaaaaaatc gtctgagagt     480
gaaaacatgg agctgaaggc ttatccccaa ttatttaaac tatgtgaaga gatgaactca     540
gaaggcttgc acaaatttat atcagacaat cgtaagaacc ttgctgtcct aaaggaagaa     600
attcctcttg cgctgaaggc tgctgcagac ccagcctgtt tggtattgga ttctctagaa     660
ggttttacc acatggaagt gtcaaatgtg atggaaaga aagattcaag cttattgggt      720
ctccgcagaa cctgtattat gttgatggaa tgccttagca ttttgttagc aaatctcaat     780
ctgaatactc ttactgctgt tatctcacaa ggtgtaaagg agcaggcaaa ggcaattgcc     840
gaagagtgga accaaagtt ggatacccctt gatgtggatg atagcaatgg gaactccttg     900
gaggctcatg ctttcctaca acttctggca acgttttcta ttgcttctga ctttaatgag     960
gaagaattat caaggctaat accaatggtc tctcgtcgtc gccaaacacc tgatttatgt    1020
cgctcccttg ggttgtcaga aaaaatgcca gtgtgcattg aagttctggt gaatagtgga    1080
aggcaaattg atgcagttaa cctagctttt gcatttgagc ttactgagca gttctctcct    1140
gtgcctttac tgaagtccta cttgaaggag gcgaaaaagg cttcttccac tgtcaaggct    1200
ggaaacatgt ctccctctgc cgagaatgag gtcaatgatc gagagctgag tgccctgaaa    1260
gctgtgatca aatgcattga agagcataac cttgaggagc agtatcccat agatcctctc    1320
caaaagcgaa ttctccagct agagaaggcc aaggccgaaa agaaagggc aactgaagtt    1380
gccaagccgc aaccaaagag accccgtgcc aatggtgctg gatacgggcc tcgagtcact    1440
aatgttgcgg ctgacaaggc attctatcct agagttgccg ataggtatcc ccaatatgtg    1500
tatgacagac cctatgttta caccggacct gctgacaacc acggcccctc tcttctgggt    1560
tctgctactt acagcttctc tcccaatcat ggcaactact ttggaaatgg ctaccagtac    1620
caagctgtcc aagccccctta tcttcactaa                                    1650
```

<210> SEQ ID NO 12
<211> LENGTH: 375
<212> TYPE: DNA
<213> ORGANISM: Citrus sinensis

<400> SEQUENCE: 12

```
atgacttgta tcattaactc cactcaatct ttagtcttgg caactgccat ggtcgtctcc      60
agcactgtcc tctttcttgc tttctccaag caaaaaaatg attctaaaga accccaagag     120
gaaacccctac gttcttgctt gtattcagag gagaagaaga aggggaggaa gaagaagagg     180
```

```
gtgcaatttg cggagaatgt gaaggacaca gctgggaacg gagaggagta caggaaagag      240
tacaacaaga aatttgcaaa acaatttgat agaacttgca gaaatgatca aattcaaggg      300
atgcccgcta ataggggtgc tttgtaccat ggaattctta gagacagagt ccacagaatg      360
gaatactcat attga                                                      375

<210> SEQ ID NO 13
<211> LENGTH: 1302
<212> TYPE: DNA
<213> ORGANISM: Citrus sinensis

<400> SEQUENCE: 13
atggaaacaa ttcacgtaaa agagtcaaca ataatacggc ctgctcaaga aaccccgaga      60
cattgcctac ggttgagtga tttagacctg ctgattccgg aaattcacat ccctgtgtg       120 tatttctacc ggcggccaaa ttatccttgc aatttcttag aaggtggttt actgaaggag      180
gctttgagta aagttcttgt cccgttttac cccttggccg gaagattggg taaagatgaa      240
aatggcagaa ttgaaataaa atgtaacgga gagggagttt atttattga agctgaaacg      300 agttgtgtcg ctgatgattt tggtgacttt gaatcaagct tcaagctcgt gcaacttgtt      360
ccacaggttg atcgcacgaa agatgcatat tttcatccac ttattatggc acaggtaact      420
cattttaagt atggaggagt ttctcttgga cttatgatgc atcatatgcc aatggacgga      480
actacggcat atcacttcat caactcatgg gctgagatgg cgcgtggcat tcctattagc      540
gttccaccaa tctttgatcg aactatacta gatgttggag tcccaacttc tccatcattt      600
caccacatcg aatacgatcc ccctccttcc atgaatactc ctactcaaaa tcctcaagcc      660
atttccaatg caatcctgaa gttatcacct gatcaaatga acatccttaa agaaaaatct      720
aagggagatc acggatccac tgtcaagtat actagatttg agattgtagc agcacatata      780
tggcgctgcg catgtaaagc acgagggttg tctgtcgatc aagctaccaa gttagagatt      840
cccacatctg ggcgatttaa attgaatcct aaaattccac ttgggtattg tggcaatgta      900
aacttcagcg ccacaccaat ggccttgtca ggtgatattc aatcggaatc gttaaattgt      960
acaacagaga gaattcatga agcaattaaa ttgagggatg acaagtatat gaagtcaggg     1020
cttgcttacc taaagcaaca acctgattta acagatgtca ggcgagacgg taaaattagt     1080
aattgtccaa acctgctgat aaccaaattg gcagacatgc ctatgtacga ggtagatctt     1140
ggatggggtc ggccggtgtt tacgacgcct tgttcggca tggacgaaga ggttttcatt      1200
ttacccggtc caaccaatga tgggagctgg tttgtggttg tagacatgga aactaaccac     1260
ttgcagcact tcaagaagta ttttatgat atctttccgt aa                        1302

<210> SEQ ID NO 14
<211> LENGTH: 125
<212> TYPE: PRT
<213> ORGANISM: Citrus sinensis

<400> SEQUENCE: 14

Met Gly Ser Lys Leu Phe Leu Leu Gly Leu Leu Met Ala Ile Ala
1               5                   10                  15

Leu Leu Ile Ser Ser Glu Val Ala Ala Arg Asp Leu Ala Glu Thr Ser
            20                  25                  30

Ile Asp His Asn Glu Lys Ala Asp Lys Ala Thr Glu Thr His Glu Ile
        35                  40                  45

Glu Asp Gly Arg Gly Gly Tyr Gly Gly Gly Gly Gly Tyr Gly Gly
```

```
                      50                  55                  60
Gly Gly Gly Tyr Gly Gly Gly Gly His Gly Gly His Gly Gly
65                  70                  75                  80

Gly His Gly Gly Gly His Gly Gly His Cys Pro Tyr Gly Cys Cys
                85                  90                  95

Gly Arg Gly Tyr Tyr Gly Arg Gly Cys Arg Cys Thr Tyr Ala Gly
                100                 105                 110

Glu Ala Val Asp Thr Glu Pro Glu Thr Glu Pro Gln Asn
                115                 120                 125

<210> SEQ ID NO 15
<211> LENGTH: 335
<212> TYPE: PRT
<213> ORGANISM: Citrus sinensis

<400> SEQUENCE: 15

Met Gly Thr Lys Ala Val Phe Leu Leu Leu Ala Leu Leu Ser Phe Ser
1               5                   10                  15

Ala Val Ser Leu Arg Ser Ala Leu Ala Glu Asn Glu Glu Asp Pro Gly
                20                  25                  30

Leu Val Met Asn Phe Tyr Lys Asp Thr Cys Pro Gln Ala Glu Asp Ile
                35                  40                  45

Ile Lys Glu Gln Val Lys Leu Leu Tyr Lys Arg His Lys Asn Thr Ala
50                  55                  60

Phe Ser Trp Leu Arg Asn Ile Phe His Asp Cys Ala Val Gln Ser Cys
65                  70                  75                  80

Asp Ala Ser Leu Leu Leu Asp Ser Thr Arg Lys Thr Leu Ser Glu Lys
                85                  90                  95

Glu Met Asp Arg Ser Phe Gly Met Arg Asn Phe Arg Tyr Ile Glu Asn
                100                 105                 110

Ile Lys Glu Ala Val Glu Arg Glu Cys Pro Gly Val Val Ser Cys Ala
                115                 120                 125

Asp Ile Leu Val Leu Ser Gly Arg Asp Gly Val Val Ala Leu Gly Gly
                130                 135                 140

Pro Tyr Ile Pro Leu Lys Thr Gly Arg Arg Asp Gly Arg Lys Ser Arg
145                 150                 155                 160

Ala Glu Ile Leu Glu Gln Tyr Leu Pro Asp His Asn Asp Ser Met Ser
                165                 170                 175

Val Val Leu Glu Arg Phe Ala Ala Ile Gly Ile Asp Ala Pro Gly Leu
                180                 185                 190

Val Ala Leu Leu Gly Ser His Ser Val Gly Arg Thr His Cys Val Lys
                195                 200                 205

Leu Val His Arg Leu Tyr Pro Glu Val Asp Pro Ala Leu Asn Pro Asp
                210                 215                 220

His Val Pro His Met Leu His Lys Cys Pro Asp Ala Ile Pro Asp Pro
225                 230                 235                 240

Lys Ala Val Gln Tyr Val Arg Asn Asp Arg Gly Thr Pro Met Val Leu
                245                 250                 255

Asp Asn Asn Tyr Tyr Arg Asn Ile Leu Asp Ser Lys Gly Leu Met Met
                260                 265                 270

Val Asp His Gln Leu Ala Thr Asp Lys Arg Thr Arg Pro Tyr Val Lys
                275                 280                 285

Lys Met Ala Lys Ser Gln Asp Tyr Phe Phe Lys Glu Phe Ser Arg Ala
                290                 295                 300
```

```
Ile Thr Ile Leu Ser Glu Asn Asn Pro Leu Thr Gly Thr Lys Gly Glu
305                 310                 315                 320

Ile Arg Lys Val Cys Asn Leu Ala Asn Lys Leu His Asp Lys Ser
                325                 330                 335

<210> SEQ ID NO 16
<211> LENGTH: 88
<212> TYPE: PRT
<213> ORGANISM: Citrus sinensis

<400> SEQUENCE: 16

Met Lys Leu Ala Leu Val Thr Phe Leu Leu Val Ser Leu Val Leu Thr
1               5                   10                  15

Ser Thr Phe Phe Glu Val Ser Met Ala Gly Ser Asp Phe Cys Asp Ser
                20                  25                  30

Lys Cys Ala Val Arg Cys Ser Lys Ala Gly Arg Glu Asp Arg Cys Leu
                35                  40                  45

Lys Tyr Cys Gly Ile Cys Cys Asp Lys Cys His Cys Val Pro Ser Gly
            50                  55                  60

Thr Tyr Gly His Lys Asp Glu Cys Pro Cys Tyr Arg Asp Leu Lys Asn
65              70                  75                  80

Ser Lys Gly Lys Pro Lys Cys Pro
                85

<210> SEQ ID NO 17
<211> LENGTH: 337
<212> TYPE: PRT
<213> ORGANISM: Citrus sinensis

<400> SEQUENCE: 17

Met Gly Asn Ser Glu Lys Asp Ser Thr Ser Lys Ser Ile Asn Glu Thr
1               5                   10                  15

Val Asn Gly Ser His Gln Phe Thr Val Lys Gly Tyr Ser Leu Ala Lys
                20                  25                  30

Gly Met Gly Pro Gly Lys Cys Leu Ser Ser Asp Val Phe Thr Val Gly
                35                  40                  45

Gly Tyr Asp Trp Ala Ile Tyr Phe Tyr Pro Asp Gly Lys Asn Pro Glu
            50                  55                  60

Asp Gly Ala Leu Tyr Val Ser Val Phe Ile Ala Leu Ala Ser Glu Gly
65              70                  75                  80

Thr Asp Val Arg Ala Leu Phe Glu Leu Thr Leu Val Asp Gln Ser Gly
                85                  90                  95

Lys Gly Lys His Lys Val His Ser His Phe Asp Arg Ala Leu Glu Ser
                100                 105                 110

Gly Pro Tyr Thr Leu Lys Tyr Arg Gly Ser Met Trp Gly Tyr Lys Arg
            115                 120                 125

Phe Phe Lys Arg Thr Ser Leu Glu Thr Ser Asp Tyr Ile Lys Asp Asp
130                 135                 140

Cys Leu Leu Ile Asn Cys Thr Val Gly Val Val Arg Asn Arg Leu Glu
145                 150                 155                 160

Gly Pro Lys Gln Tyr Ser Ile Pro Val Pro Pro Ser Asp Met Gly Gln
                165                 170                 175

Gly Leu Lys Asp Leu Leu Glu Ser Glu Ile Gly Cys Asp Ile Val Phe
            180                 185                 190

Glu Val Gly Asp Glu Thr Phe Lys Ala His Lys Leu Ile Leu Ala Ala
            195                 200                 205
```

```
Arg Ser Pro Val Phe Arg Ala Gln Phe Tyr Gly Leu Val Gly Asp Arg
    210                 215                 220
Asn Leu Asp Lys Val Val Val Lys Asp Val Glu Pro Ser Ile Phe Lys
225                 230                 235                 240
Ala Met Leu Leu Phe Ile Tyr Thr Asp Lys Phe Pro Asp Val Tyr Glu
                245                 250                 255
Ile Thr Gly Thr Thr Ser Met Cys Thr Thr Asn Met Val Gln His
                260                 265                 270
Leu Leu Ala Ala Ala Asp Leu Tyr Asn Val Asp Arg Leu Lys Leu Leu
                275                 280                 285
Cys Glu Ser Lys Leu Cys Glu Glu Leu Asn Ala Glu Thr Val Ala Thr
290                 295                 300
Thr Leu Ala Leu Ala Glu Gln His Gln Cys Pro Gln Leu Lys Ala Ile
305                 310                 315                 320
Cys Leu Lys Phe Ala Ala Thr Pro Ala Asn Leu Gly Gly Ala Cys Cys
                325                 330                 335
Ser

<210> SEQ ID NO 18
<211> LENGTH: 342
<212> TYPE: PRT
<213> ORGANISM: Citrus sinensis

<400> SEQUENCE: 18

Met Lys Met Glu Ser Ser Glu Leu Ile Pro Ser Leu Pro Glu Glu Leu
1               5                   10                  15
Ser Leu Glu Cys Leu Thr Arg Leu Pro Tyr Ser Thr His Arg Leu Ala
                20                  25                  30
Ser Ala Val Cys Arg Arg Trp Arg Gln Leu Leu Gln Ser Gln Asp Phe
                35                  40                  45
Tyr Tyr Gln Arg Lys Asn Ser Gly His Thr His Lys Val Ala Cys Leu
    50                  55                  60
Val Gln Ala Glu Lys Glu Ser Asp Gly Gly Lys Lys Pro Gly Glu Ser
65                  70                  75                  80
Pro Ser Tyr Arg Leu Ser Val Phe Asp Arg Val Gly Ala Val Trp Asp
                85                  90                  95
Arg Ile Asp Pro Val Pro Gly Tyr Pro Asn Gly Leu Pro Leu Phe Cys
                100                 105                 110
Gln Leu Ala Gly Cys Lys Gly Lys Leu Val Val Met Gly Gly Trp Asp
            115                 120                 125
Pro Asp Ser Tyr Asn Pro Val Thr Asp Val Phe Val Tyr Asp Phe Gly
        130                 135                 140
Met Arg Arg Trp Arg Lys Gly Lys Asp Leu Pro Ala Lys Met Ser Phe
145                 150                 155                 160
Phe Gly Cys Gly Ser Ala Glu Gly Arg Val Tyr Val Ala Gly Gly His
                165                 170                 175
Asp Gln Asn Lys Asn Ala Leu Arg Thr Gly Trp Val Tyr Asp Leu Arg
            180                 185                 190
Arg Asp Glu Trp Ser Glu Leu Thr Gln Leu Ser Gln Glu Arg Asp Glu
        195                 200                 205
Cys Glu Gly Val Val Ile Gly Asp Glu Phe Trp Val Ile Ser Gly Tyr
    210                 215                 220
Asn Thr Glu Asn Gln Gly Ala Phe Asp Gly Ser Ala Asp Ala Tyr Gly
225                 230                 235                 240
```

```
Phe Gly Ser Gly Gln Trp Lys Arg Val Glu Gly Ile Trp Glu Ala Gly
                245                 250                 255

Arg Cys Pro Arg Ser Asn Val Gly Val Gly Lys Asp Gly Arg Ile Phe
            260                 265                 270

Ser Trp Ser Glu Leu Asp Ser Val Arg Ala Gly Leu Cys Gly Val
        275                 280                 285

Ala Leu Gly Asp Arg Val Leu Val Thr Gly Ser Glu Tyr Gln Gly Ala
    290                 295                 300

Pro Ser Gly Phe Tyr Leu Ala Glu Ile Gly Gly Gln Lys Val Lys
305                 310                 315                 320

Leu Glu Lys Ile Asn Val Pro Asp Glu Phe Ser Gly Phe Val Gln Ser
                325                 330                 335

Gly Cys Cys Val Glu Ile
            340

<210> SEQ ID NO 19
<211> LENGTH: 229
<212> TYPE: PRT
<213> ORGANISM: Citrus sinensis

<400> SEQUENCE: 19

Met Leu Gly Val Phe Ser Ser Ala Ile Val Ser Pro Pro Glu Glu Leu
1               5                   10                  15

Val Ala Ala Gly Ser Arg Thr Pro Ser Pro Lys Thr Thr Ser Thr Ala
            20                  25                  30

Leu Val Asp Arg Phe Leu Gln Ala Asn Ser Ser Ala Val Ser Val Gln
        35                  40                  45

Val Gly Asp Asn Val Thr Leu Ala Tyr Thr His Gln Asn Glu Ser Pro
    50                  55                  60

Leu Arg Gln Arg Ser Phe Ala Val Lys Asp Glu Ile Phe Cys Leu Phe
65                  70                  75                  80

Glu Gly Ala Leu Asp Asn Leu Gly Ser Leu Arg Gln Gln Tyr Gly Leu
                85                  90                  95

Ala Lys Ser Ala Asn Glu Val Ile Leu Val Ile Glu Ala Tyr Lys Ala
            100                 105                 110

Leu Arg Asp Arg Ala Pro Tyr Pro Pro Asn His Val Gly His Leu
        115                 120                 125

Ser Gly Tyr Phe Ala Phe Ile Val Tyr Asp Lys Ser Thr Ser Thr Leu
    130                 135                 140

Phe Val Ala Ser Asp Gln Phe Gly Lys Val Pro Leu Tyr Trp Gly Ile
145                 150                 155                 160

Thr Ala Asp Gly His Val Ala Phe Ala Asp Asp Ala Asp Leu Leu Lys
                165                 170                 175

Gly Ala Cys Gly Lys Ser Leu Ala Ser Phe Pro Gln Gly Cys Phe Phe
            180                 185                 190

Ser Thr Ala Val Gly Gly Leu Arg Ser Phe Glu Asn Pro Lys Asn Lys
        195                 200                 205

Ile Thr Ala Val Pro Ala Ala Glu Glu Ile Trp Gly Ala Thr Phe
    210                 215                 220

Lys Val Met Ser Ser
225

<210> SEQ ID NO 20
<211> LENGTH: 161
<212> TYPE: PRT
<213> ORGANISM: Citrus sinensis
```

<400> SEQUENCE: 20

Met Asn Arg Cys Ala Val Met Gly Leu Gly Gly Gly Cys Asp Glu Glu
1               5                   10                  15

Arg Arg Met Gly Ser Met Ile Cys Pro Lys Pro Arg Arg Leu Gly Leu
            20                  25                  30

Ile Asn Pro Pro Ile Asn Asp Ser Ile Arg His Leu Lys Arg Pro Ala
        35                  40                  45

Ser Glu Phe Gly Asp Ser Lys Ala Gly Thr Glu Leu Leu Asp Leu Ile
    50                  55                  60

Leu Thr Lys Gly Gly Tyr Gly Thr Glu Lys Thr Gly Asn Gln Val Ala
65              70                  75                  80

Ser Ser Pro Pro Tyr Phe Ser Gly Ser Pro Ser Arg Ala Ser Asn
                85                  90                  95

Pro Leu Ile Gln Asp Ala Gln Phe Gly Asn Glu Lys Ser Ala Pro Leu
            100                 105                 110

Thr Ala Ala Pro Pro Ser Pro Ser Arg Met Gly Gly Gly Cys
        115                 120                 125

Val Arg Val Lys Phe Gly His Lys Pro Ala Ala Val Arg Ile Glu Gly
130                 135                 140

Phe Asp Cys Leu Ser Arg Asp Arg Arg Asn Cys Ser Ile Ser Ala Val
145                 150                 155                 160

Ala

<210> SEQ ID NO 21
<211> LENGTH: 304
<212> TYPE: PRT
<213> ORGANISM: Citrus sinensis

<400> SEQUENCE: 21

Met Thr Ile Leu Ile Asp Gln Pro His Phe Gly Val Glu Val Gln Glu
1               5                   10                  15

Lys Lys Val Pro Ile Asp Glu Lys Glu Leu Ser Leu Asp Gly Gly Phe
            20                  25                  30

Leu Val Pro Gln Thr Asn Ser Phe Gly His Thr Phe Arg Asp Tyr Asp
        35                  40                  45

Ala Glu Gly Glu Arg Gln Glu Gly Val Glu Asn Phe Arg Ile Asn
    50                  55                  60

His Ile Asn Gln Thr Tyr Asp Phe Val Lys Lys Met Arg Glu Glu Tyr
65              70                  75                  80

Gly Lys Leu Asn Arg Val Glu Met Ser Ile Trp Glu Cys Cys Glu Leu
                85                  90                  95

Leu Asn Asp Val Val Asp Glu Ser Asp Pro Asp Leu Asp Glu Pro Gln
            100                 105                 110

Ile Glu His Leu Leu Gln Thr Ala Glu Ala Ile Arg Lys Asp Tyr Pro
        115                 120                 125

Asp Glu Asp Trp Leu His Leu Thr Gly Leu Ile His Asp Leu Gly Lys
    130                 135                 140

Val Leu Asn Leu Pro Ser Phe Gly Gly Leu Pro Gln Trp Ala Val Val
145                 150                 155                 160

Gly Asp Thr Phe Pro Val Gly Cys Ala Phe Asp Glu Ser Ile Val His
                165                 170                 175

His Lys Tyr Phe Lys Glu Asn Pro Asp Tyr Ser Asn Pro Ala Phe Asn
            180                 185                 190

```
Thr Glu Tyr Gly Val Tyr Ser Glu Gly Cys Gly Leu Asp Asn Val Met
            195                 200                 205
Met Ser Trp Gly His Asp Asp Tyr Met Tyr Leu Val Ala Asn Glu Asn
    210                 215                 220
Lys Thr Thr Leu Pro Ser Ala Ala Leu Leu Ile Ile Arg Tyr His Ser
225                 230                 235                 240
Phe His Ala Leu His Lys Ser Glu Ala Tyr Lys Asn Leu Met Asn Glu
                245                 250                 255
Glu Asp Val Glu Asn Leu Lys Trp Leu Gln Ile Phe Ser Lys Tyr Asp
            260                 265                 270
Leu Tyr Ser Lys Ser Lys Val Arg Ile Asp Val Glu Lys Val Lys Pro
    275                 280                 285
Tyr Tyr Leu Ser Leu Ile Glu Lys Tyr Phe Leu Ala Lys Leu Lys Trp
290                 295                 300

<210> SEQ ID NO 22
<211> LENGTH: 253
<212> TYPE: PRT
<213> ORGANISM: Citrus sinensis

<400> SEQUENCE: 22

Met Cys Gly Gly Ala Leu Ile Ala Asp Tyr Asp Glu Val Arg Pro Val
1               5                   10                  15
Arg Arg Glu Arg Lys Leu Thr Ser Glu Asp Leu Trp Ser Glu Phe Gly
            20                  25                  30
Ser Ile Ser Asp Leu Leu Gly Leu Asp Tyr Asn Gly Lys Ser His Pro
        35                  40                  45
Lys Gln Pro Leu Lys Val Lys Asn Glu Lys Ala Glu Asp Ser Ser Asn
50                  55                  60
Lys Ala Ala Arg Val Glu Gly Lys Glu Lys Thr Gln Arg Val Arg
65                  70                  75                  80
Lys Asn Val Tyr Arg Gly Ile Arg Gln Arg Pro Trp Gly Lys Trp Ala
                85                  90                  95
Ala Glu Ile Arg Asp Pro Tyr Lys Gly Val Arg Val Trp Leu Gly Thr
            100                 105                 110
Phe Asn Thr Ala Glu Glu Ala Ala Arg Ala Tyr Asp Glu Ala Ala Lys
        115                 120                 125
Arg Ile Arg Gly Asp Lys Ala Lys Leu Asn Phe Ala Gln Pro Pro
130                 135                 140
Pro Ile Ala Pro Pro Ala Lys Lys Arg Cys Met Pro Ser Pro Glu
145                 150                 155                 160
Leu Thr Gln Pro Arg Phe Glu Thr Ile Gly Thr Pro Ala Pro Ala
                165                 170                 175
Pro Ser Pro Trp Val Gly Phe Gly Tyr Gln Asn Glu Phe Tyr Gln Pro
            180                 185                 190
Arg Ala Val Asp Asp Glu Phe Glu Leu Ser Gln Gln Ile Ser Ser Leu
        195                 200                 205
Glu Ser Phe Leu Gly Leu Glu Pro Leu Met Ser Gln Pro Ser Gly Asn
    210                 215                 220
Gly Ala Gly Gly Tyr Asp Ser Val Asp Phe Trp Met Leu Asp Asp Val
225                 230                 235                 240
Ala Ala Thr Gln Gln Leu Asn Ser Asn Gln Phe Leu Cys
                245                 250

<210> SEQ ID NO 23
```

<211> LENGTH: 248
<212> TYPE: PRT
<213> ORGANISM: Citrus sinensis

<400> SEQUENCE: 23

```
Met Gln Leu Ser Thr Asn Phe Thr Ala Ser Pro Phe Arg Ser Gln Asn
1               5                   10                  15

His Leu Phe Asn Asn Leu Ser Pro Thr Ser Phe Leu His Lys Ser Leu
            20                  25                  30

Phe Leu Ser Arg Pro Thr Lys Thr Leu Gln Asn Leu Leu Phe Ser Asn
        35                  40                  45

Pro Lys Ser Ser Gln Lys Lys Leu Leu Arg Thr Ser Thr Ile Asn Ala
    50                  55                  60

Ser Leu Leu Glu Ala Pro Leu Leu Trp Ala Gly Arg Leu Cys Val Tyr
65                  70                  75                  80

Tyr Ala Leu Leu Lys Ala Gly Leu Ala Gly Ser Gln Ala Asn Pro Leu
                85                  90                  95

Val Ser Asp Leu Glu Ser Gly Gly Val Thr Gly Ser Glu Gly Ala Asp
            100                 105                 110

Leu Gly Phe Ser Lys Trp Leu Glu Asn Ile Lys Gly Lys Pro Asp Lys
        115                 120                 125

Glu Ala Ala Asp Lys Arg Lys Leu Val Ser Lys Trp His Pro Thr Thr
    130                 135                 140

Lys Gly Thr Leu Arg Arg Asn Tyr Arg Val Pro Ser Lys Ser Glu Gly
145                 150                 155                 160

Arg Arg Leu Leu Lys Ala Ile Ala Ser Leu Leu Ser Asp Asp His
                165                 170                 175

Phe Thr Asp Ala Thr Ser His Lys Gly Cys Gln Ile Arg Arg Glu Asn
            180                 185                 190

Val His Gly Glu Ser Val Cys Cys Asn Asn Val Arg Ala Leu Phe Asp
        195                 200                 205

Glu Leu Pro Thr Pro His Leu Val Val Glu Ile Thr Pro Phe Pro Ala
    210                 215                 220

Gly Pro Leu Thr Glu Lys Asp Tyr Val Lys Ala Glu Lys Leu Glu Arg
225                 230                 235                 240

Val Leu Arg Ser Gly Pro Ser Ile
                245
```

<210> SEQ ID NO 24
<211> LENGTH: 549
<212> TYPE: PRT
<213> ORGANISM: Citrus sinensis

<400> SEQUENCE: 24

```
Met Glu Glu Asn Gln Ser Val Ala Thr Leu Met Asp Ser Thr Thr Ser
1               5                   10                  15

Lys Ile Gln Gln Leu Gln Lys Ala Phe Ala Glu Leu Glu Ser His Arg
            20                  25                  30

Ala Ile Thr Leu Asn Leu Arg Trp Lys Glu Leu Glu Glu His Phe His
        35                  40                  45

Gly Leu Glu Lys Ser Leu Lys Arg Arg Phe His Glu Leu Glu Asp Gln
    50                  55                  60

Glu Lys Glu Phe Glu Thr Lys Thr Arg Lys Ala Arg Glu Ile Leu Gln
65                  70                  75                  80
```

-continued

```
Lys Arg Glu Ala Ala Val Leu Ala Lys Glu Gln Thr Thr Leu Glu Lys
                85                  90                  95

Leu Gln Lys Lys Arg Asp Ala Ala Val Phe Ala Ile Ser Thr Ala Leu
            100                 105                 110

Glu Lys Gln Arg Lys Val Ser Ser Ala Glu Pro Ala Ile Val Ser Asn
        115                 120                 125

Val Asp Glu Ser Arg Ala Pro Pro Val Glu Asp Lys Leu Pro Asp Ser
    130                 135                 140

Met Ser Leu Glu Asn Asn Leu Glu Ser Ser Lys Lys Ser Ser Glu Ser
145                 150                 155                 160

Glu Asn Met Glu Leu Lys Ala Tyr Pro Gln Leu Phe Lys Leu Cys Glu
                165                 170                 175

Glu Met Asn Ser Glu Gly Leu His Lys Phe Ile Ser Asp Asn Arg Lys
            180                 185                 190

Asn Leu Ala Val Leu Lys Glu Glu Ile Pro Leu Ala Leu Lys Ala Ala
        195                 200                 205

Ala Asp Pro Ala Cys Leu Val Leu Asp Ser Leu Glu Gly Phe Tyr His
    210                 215                 220

Met Glu Val Ser Asn Val Asp Gly Lys Lys Asp Ser Ser Leu Leu Gly
225                 230                 235                 240

Leu Arg Arg Thr Cys Ile Met Leu Met Glu Cys Leu Ser Ile Leu Leu
                245                 250                 255

Ala Asn Leu Asn Leu Asn Thr Leu Thr Ala Val Ile Ser Gln Gly Val
            260                 265                 270

Lys Glu Gln Ala Lys Ala Ile Ala Glu Glu Trp Lys Pro Lys Leu Asp
        275                 280                 285

Thr Leu Asp Val Asp Asp Ser Asn Gly Asn Ser Leu Glu Ala His Ala
    290                 295                 300

Phe Leu Gln Leu Leu Ala Thr Phe Ser Ile Ala Ser Asp Phe Asn Glu
305                 310                 315                 320

Glu Glu Leu Ser Arg Leu Ile Pro Met Val Ser Arg Arg Gln Thr
                325                 330                 335

Pro Asp Leu Cys Arg Ser Leu Gly Leu Ser Glu Lys Met Pro Gly Val
            340                 345                 350

Ile Glu Val Leu Val Asn Ser Gly Arg Gln Ile Asp Ala Val Asn Leu
        355                 360                 365

Ala Phe Ala Phe Glu Leu Thr Glu Gln Phe Ser Pro Val Pro Leu Leu
    370                 375                 380

Lys Ser Tyr Leu Lys Glu Ala Lys Lys Ala Ser Ser Thr Val Lys Ala
385                 390                 395                 400

Gly Asn Met Ser Pro Ser Ala Glu Asn Glu Val Asn Asp Arg Glu Leu
                405                 410                 415

Ser Ala Leu Lys Ala Val Ile Lys Cys Ile Glu Glu His Asn Leu Glu
            420                 425                 430

Glu Gln Tyr Pro Ile Asp Pro Leu Gln Lys Arg Ile Leu Gln Leu Glu
        435                 440                 445

Lys Ala Lys Ala Glu Lys Lys Arg Ala Thr Glu Val Ala Lys Pro Gln
    450                 455                 460

Pro Lys Arg Pro Arg Ala Asn Gly Ala Gly Tyr Gly Pro Arg Val Thr
465                 470                 475                 480
```

-continued

```
Asn Val Ala Ala Asp Lys Ala Phe Tyr Pro Arg Val Ala Asp Arg Tyr
            485                 490                 495

Pro Gln Tyr Val Tyr Asp Arg Pro Tyr Val Tyr Thr Gly Pro Ala Asp
        500                 505                 510

Asn His Gly Pro Ser Leu Leu Gly Ser Ala Thr Tyr Ser Phe Ser Pro
        515                 520                 525

Asn His Gly Asn Tyr Phe Gly Asn Gly Tyr Gln Tyr Gln Ala Val Gln
        530                 535                 540

Ala Pro Tyr Leu His
545

<210> SEQ ID NO 25
<211> LENGTH: 124
<212> TYPE: PRT
<213> ORGANISM: Citrus sinensis

<400> SEQUENCE: 25

Met Thr Cys Ile Ile Asn Ser Thr Gln Ser Leu Val Leu Ala Thr Ala
1               5                   10                  15

Met Val Val Ser Ser Thr Val Leu Phe Leu Ala Phe Ser Lys Gln Lys
            20                  25                  30

Asn Asp Ser Lys Glu Pro Gln Glu Glu Thr Leu Arg Ser Cys Leu Tyr
        35                  40                  45

Ser Glu Glu Lys Lys Lys Gly Arg Lys Lys Arg Val Gln Phe Ala
    50                  55                  60

Glu Asn Val Lys Asp Thr Ala Gly Asn Gly Glu Glu Tyr Arg Lys Glu
65                  70                  75                  80

Tyr Asn Lys Lys Phe Ala Lys Gln Phe Asp Arg Thr Cys Arg Asn Asp
                85                  90                  95

Gln Ile Gln Gly Met Pro Ala Asn Arg Val Ala Leu Tyr His Gly Ile
            100                 105                 110

Leu Arg Asp Arg Val His Arg Met Glu Tyr Ser Tyr
        115                 120

<210> SEQ ID NO 26
<211> LENGTH: 433
<212> TYPE: PRT
<213> ORGANISM: Citrus sinensis

<400> SEQUENCE: 26

Met Glu Thr Ile His Val Lys Glu Ser Thr Ile Ile Arg Pro Ala Gln
1               5                   10                  15

Glu Thr Pro Arg His Cys Leu Arg Leu Ser Asp Leu Asp Leu Leu Ile
            20                  25                  30

Pro Glu Ile His Ile Pro Cys Val Tyr Phe Tyr Arg Arg Pro Asn Tyr
        35                  40                  45

Pro Cys Asn Phe Leu Glu Gly Leu Leu Lys Glu Ala Leu Ser Lys
    50                  55                  60

Val Leu Val Pro Phe Tyr Pro Leu Ala Gly Arg Leu Gly Lys Asp Glu
65                  70                  75                  80

Asn Gly Arg Ile Glu Ile Lys Cys Asn Gly Glu Gly Val Leu Phe Ile
                85                  90                  95

Glu Ala Glu Thr Ser Cys Val Ala Asp Asp Phe Gly Asp Phe Glu Ser
            100                 105                 110
```

```
Ser Phe Lys Leu Val Gln Leu Val Pro Gln Val Asp Arg Thr Lys Asp
            115                 120                 125

Ala Tyr Phe His Pro Leu Ile Met Ala Gln Val Thr His Phe Lys Tyr
    130                 135                 140

Gly Gly Val Ser Leu Gly Leu Met Met His Met Pro Met Asp Gly
145                 150                 155                 160

Thr Thr Ala Tyr His Phe Ile Asn Ser Trp Ala Glu Met Ala Arg Gly
                165                 170                 175

Ile Pro Ile Ser Val Pro Pro Ile Phe Asp Arg Thr Ile Leu Asp Val
            180                 185                 190

Gly Val Pro Thr Ser Pro Ser Phe His His Ile Glu Tyr Asp Pro Pro
            195                 200                 205

Pro Ser Met Asn Thr Pro Thr Gln Asn Pro Gln Ala Ile Ser Asn Ala
    210                 215                 220

Ile Leu Lys Leu Ser Pro Asp Gln Met Asn Ile Leu Lys Glu Lys Ser
225                 230                 235                 240

Lys Gly Asp His Gly Ser Thr Val Lys Tyr Thr Arg Phe Glu Ile Val
                245                 250                 255

Ala Ala His Ile Trp Arg Cys Ala Cys Lys Ala Arg Gly Leu Ser Val
            260                 265                 270

Asp Gln Ala Thr Lys Leu Glu Ile Pro Thr Ser Gly Arg Phe Lys Leu
    275                 280                 285

Asn Pro Lys Ile Pro Leu Gly Tyr Cys Gly Asn Val Asn Phe Ser Ala
    290                 295                 300

Thr Pro Met Ala Leu Ser Gly Asp Ile Gln Ser Glu Ser Leu Asn Cys
305                 310                 315                 320

Thr Thr Glu Arg Ile His Glu Ala Ile Lys Leu Arg Asp Asp Lys Tyr
                325                 330                 335

Met Lys Ser Gly Leu Ala Tyr Leu Lys Gln Gln Pro Asp Leu Thr Asp
            340                 345                 350

Val Arg Arg Asp Gly Lys Ile Ser Asn Cys Pro Asn Leu Leu Ile Thr
    355                 360                 365

Lys Leu Ala Asp Met Pro Met Tyr Glu Val Asp Leu Gly Trp Gly Arg
370                 375                 380

Pro Val Phe Thr Thr Pro Leu Phe Gly Met Asp Glu Glu Val Phe Ile
385                 390                 395                 400

Leu Pro Gly Pro Thr Asn Asp Gly Ser Trp Phe Val Val Asp Met
                405                 410                 415

Glu Thr Asn His Leu Gln His Phe Lys Lys Tyr Phe Tyr Asp Ile Phe
            420                 425                 430

Pro

<210> SEQ ID NO 27
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, c, t, g, unknown or other

<400> SEQUENCE: 27
ggtctcnnnn n                                                        11
```